(12) United States Patent
Rodriguez et al.

(10) Patent No.: US 8,859,287 B2
(45) Date of Patent: Oct. 14, 2014

(54) COMPOSITIONS AND METHODS FOR TREATMENT OF CANCER USING TISSUE-SPECIFIC ONCOLYTIC ADENOVIRUSES

(75) Inventors: Ronald Rodriguez, Glenwood, MD (US); Naser Uddin Hoti, Baltimore, MD (US)

(73) Assignee: The Johns Hopkins University, Baltimore, MD (US)

( * ) Notice: Subject to any disclaimer, the term of this patent is extended or adjusted under 35 U.S.C. 154(b) by 0 days.

(21) Appl. No.: 13/511,878

(22) PCT Filed: Dec. 2, 2010

(86) PCT No.: PCT/US2010/058626
§ 371 (c)(1),
(2), (4) Date: Aug. 15, 2012

(87) PCT Pub. No.: WO2011/068918
PCT Pub. Date: Jun. 9, 2011

(65) Prior Publication Data
US 2012/0308521 A1    Dec. 6, 2012

Related U.S. Application Data

(60) Provisional application No. 61/265,985, filed on Dec. 2, 2009.

(51) Int. Cl.
*C12N 15/00* (2006.01)
*C12N 15/113* (2010.01)
*A61K 35/76* (2006.01)

(52) U.S. Cl.
CPC .. *C12N 15/1135* (2013.01); *C12N 2710/10332* (2013.01); *C12N 2310/531* (2013.01); *A61K 35/761* (2013.01)
USPC .......................................... 435/455

(58) Field of Classification Search
USPC .......................................... 435/455
See application file for complete search history.

(56) References Cited

U.S. PATENT DOCUMENTS

| | | | |
|---|---|---|---|
| 7,763,722 B2 | 7/2010 | Chang | |
| 2006/0269518 A1 | 11/2006 | Chang | |
| 2008/0247996 A1* | 10/2008 | Yu et al. | 424/93.2 |
| 2009/0074658 A1* | 3/2009 | Lupold et al. | 424/1.11 |
| 2011/0054009 A1* | 3/2011 | Croce et al. | 514/44 A |

OTHER PUBLICATIONS

Haferkamp et al., "The Relative Contributions of the p53 and pRb Pathways in Oncogene-Induced Melanocyte Senescence," *Aging* (2009), 1(6):542-556.

* cited by examiner

*Primary Examiner* — Brian Whiteman
(74) *Attorney, Agent, or Firm* — DLA Piper LLP (US)

(57) ABSTRACT

The present invention includes the use of a nucleic acid sequence encoding an shRNA to target RNA interference against a cellular factor where such use can enhance oncolytic adenovius replication. The nucleic acid sequence encoding an shRNA can be introduced into an oncolytic adenovius construct via a recombination event, and such nucleic acid sequence encoding an shRNA can reside in either the E1 region or Fiber region of the oncolytic adenovius construct. In particular, the oncolytic adenovius construct optionally include a prostate specific promoter or prostate specific enhancer for issue specific expression in prostate cancer cells. The oncolytic adenovius constructs of the invention provides utility for the treatment of cancers, in particular prostate cancer.

13 Claims, 26 Drawing Sheets

Ad5-RV004

Ad5-RV004.21

SEQUENCE LISTING

```
<160> NUMBER OF SEQ ID NOS: 6

<210> SEQ ID NO 1
<211> LENGTH: 64
<212> TYPE: DNA
<213> ORGANISM: Artificial Sequence
<220> FEATURE:
<223> OTHER INFORMATION: Synthetic construct

<400> SEQUENCE: 1
gatccccagc gatggaactt cgactttca agagaaagtc gaagttccat cgcttttttg     60
gaac                                                                 64

<210> SEQ ID NO 2
<211> LENGTH: 64
<212> TYPE: RNA
<213> ORGANISM: Artificial Sequence
<220> FEATURE:
```

-continued

```
<223> OTHER INFORMATION: Synthetic construct

<400> SEQUENCE: 2 gaucccagc gauggaacuu cgacuuuuca agagaaaguc gaaguuccau cgcuuuuug      60 gaac                                                                 64

<210> SEQ ID NO 3
<211> LENGTH: 19
<212> TYPE: DNA
<213> ORGANISM: Artificial Sequence
<220> FEATURE:
<223> OTHER INFORMATION: Primer

<400> SEQUENCE: 3
cgttccgggt caaagttgg                                                 19

<210> SEQ ID NO 4
<211> LENGTH: 22
<212> TYPE: DNA
<213> ORGANISM: Artificial Sequence
<220> FEATURE:
<223> OTHER INFORMATION: Primer

<400> SEQUENCE: 4
cctccgtggc agataatatg tc                                             22

<210> SEQ ID NO 5
<211> LENGTH: 18
<212> TYPE: DNA
<213> ORGANISM: Artificial Sequence
<220> FEATURE:
<223> OTHER INFORMATION: Primer

<400> SEQUENCE: 5
gaacgctgac gtcatcaa                                                  18

<210> SEQ ID NO 6
<211> LENGTH: 16
<212> TYPE: DNA
<213> ORGANISM: Artificial Sequence
<220> FEATURE:
<223> OTHER INFORMATION: Primer

<400> SEQUENCE: 6
aagttccatc gctggg                                                    16
```

COMPOSITIONS AND METHODS FOR TREATMENT OF CANCER USING TISSUE-SPECIFIC ONCOLYTIC ADENOVIRUSES

CROSS-REFERENCE TO RELATED APPLICATIONS

This application is a 35 USC §371 National Stage application of International Application No. PCT/US2010/058626 filed Dec. 2, 2010, now pending; which claims the benefit under 35 USC §119(e) to U.S. application Ser. No. 61/265,985 filed Dec. 2, 2009, now expired. The disclosure of each of the prior applications is considered part of and is incorporated by reference in the disclosure of this application.

GRANT INFORMATION

This invention was made with government support under Grant No. RO1/1R01CA121153-01A2 awarded by the National Institutes of Health, National Cancer Institute. The government has certain rights in the invention.

BACKGROUND OF THE INVENTION

1. Field of the Invention

The invention relates generally to oncolytic virus for cancer treatment and more specifically to the use of RNA interference mechanism in a modified oncolytic adenovirus for treatment of cancers including prostate cancer.

2. Background Information

Despite escalating research efforts for treatment of prostate cancer, advanced prostate cancer (PCa) remains incurable. Traditional chemotherapeutic strategies do provide some benefits by nominally extending life expectancy (less than 2.5 months) for hormone resistant disease, yet resistance to such therapies remains a serious clinical problem. One strategy for approaching this recalcitrant disease has been the development of prostate-specific conditionally replicating adenoviruses (CRAds). Prostate-specific CRAds are generated by placing the adenoviral genes responsible for controlling replication (E1A, E1B, or E4) under the control of a prostate-specific promoter. Early prostate-specific CRAds utilized the PSA promoter and enhancer to control E1A expression or the rat probasin promoter to control E1A plus the PSA promoter and enhancer to control E1B. Although this strategy has shown clinical efficacy in early phase trials, the potency of these viruses has been inadequate to be considered for a single modality therapy.

Adenoviruses infect both quiescent and non quiescent cells and are known to replicate their genome inside the host cell nucleus. However, once inside the host cell the virus needs to overcome multiple challenges before it can propagate its progeny. Besides tumor suppressors like p53 and Rb, cell cycle regulation is one of the hindrances that the virus encounters. Adenoviruses have evolved multiple methods that help overcome these barriers. It is now believed that the immediate adenovirus early gene, E1A, regulates the expression of host and viral genes and creates a cellular environment favorable for viral replication. Based on the importance of E1A in adenoviral biology, the majority of adeno-gene therapy vectors rely on either replacing E1A gene from the virus backbone with the gene of interest or using tissue/cancer specific promoters to limit viral replication to specific tissues and organs. Although these manipulations helped in restricting viral replication to the tissue of interest, using promoters other than the endogenous viral promoters attenuates its replication potential and therefore compromise viral cytotoxicity.

Therefore, there remains a need for modified and improved oncolytic viruses for the treatment of cancers, in particular prostate cancer.

SUMMARY OF THE INVENTION

The present invention is based on the seminal discovery that the use of a nucleic acid sequence encoding an shRNA to target RNA interference against a cellular factor where such use can enhance oncolytic adenovius replication. The nucleic acid sequence encoding an shRNA can be introduced into an oncolytic adenovius construct via a recombination event, and such nucleic acid sequence encoding an shRNA can reside in either the E1 region or Fiber region of the oncolytic adenovius construct. In particular, the oncolytic adenovius construct optionally include a prostate specific promoter or prostate specific enhancer for issue specific expression in prostate cancer cells. The oncolytic adenovius constructs of the invention provides utility for the treatment of cancers, in particular prostate cancer.

In one embodiment, the present invention provides an oncolytic adenovirus construct for treatment of prostate cancer. The oncolytic adenovirus construct includes a nucleic acid sequence encoding an shRNA in the E1 region or the Fiber region, and optionally a nucleic acid sequence encoding a tissue specific promoter or a tissue specific enhancer. In one aspect, the shRNA is targeted to RNA interference against p21/Waf-1. In an additional aspect, the shRNA includes a nucleic acid sequence of SEQ ID NO:1 5'-GATCCCCAGC-GATGGAACTTCGACTTTTCAA-GAGAAAGTCGAAGTTCCATCGCTT TTTTGGAAC-3' or SEQ ID NO:2 5'-GAUCCCCAGCGAUGGAACUUC-GACUUUUCAAGAGAAAGUCGAAGUUCCAUCGC UUUUUUGGAAC-3'. In another aspect, the tissue specific promoter is a prostate specific promoter. In another aspect, the tissue specific enhancer is a prostate specific enhancer.

In another embodiment, the present invention provides a pharmaceutical composition including an adenovirus construct provided herein and a pharmaceutically acceptable carrier. In another embodiment, the present invention provides a method for enhancing oncolytic adenovirus replication in prostate cells. The method includes contacting the prostate cells with an adenovirus construct provided herein. In one aspect, the prostate cells are exposed to a radiation treatment prior to, simultaneous with or following contact with the adenovirus construct. In another embodiment, the present invention provides a method for enhancing oncolytic adenovirus replication in prostate cells. The method includes contacting the prostate cells with a composition provided herein. In one aspect, the prostate cells are exposed to a radiation treatment prior to, simultaneous with or following contact with the composition.

In another embodiment, the present invention provides a method for treating a subject having prostate cancer. The method includes administering to the subject a therapeutically effective amount of an adenovirus construct provided herein. In one aspect, the subject is exposed to a radiation treatment prior to, simultaneous with or following contact with the adenovirus construct. In another embodiment, the present invention provides a method for treating a subject having prostate cancer. The method includes administering to the subject a therapeutically effective amount of a composition provided herein. In one aspect, the subject is exposed to a radiation treatment prior to, simultaneous with or following contact with the composition. In various aspects, the subject is a human patient.

In another embodiment, the present invention provides a method for selectively lysing a neoplastic prostate cell. The method includes contacting the cell with an effective amount of an adenovirus construct provided herein. In one aspect, the cell is exposed to a radiation treatment prior to, simultaneous with or following contact with the adenovirus construct. In another embodiment, the present invention provides a method for selectively lysing a neoplastic prostate cell. The method includes contacting the cell with an effective amount of a composition provided herein. In one aspect, the cell is exposed to a radiation treatment prior to, simultaneous with or following contact with a composition.

In another embodiment, the present invention provides a method for prognosis for a prostate cancer treatment. The method includes (a) contacting prostate cancer cells with an adenovirus construct provided herein; (b) measuring at least one of the following:
  (i) size of the prostate;
  (ii) size of the prostate cancer;
  (iii) blood level of prostate-specific antigen (PSA);
  (iii) blood level of sex hormones;
  (iv) thymosin β15 levels;
  (v) phosphorylation level of NF-κB-p65/RelA at 254th amino acid threonine; and
  (vi) mRNA level of PSA or PCA3; and
  (c) correlating measurement of (b) with the prognosis for the prostate cancer treatment.

In one aspect, a specific antibody is used for the method above. In an additiona aspect, ELISA or Western blotting is used for the method above. In another aspect, quantitative PCR or Northern blotting is used for the method above. In another aspect, the prostate cancer cells are exposed to a radiation treatment prior to, simultaneous with or following contact with the adenovirus construct.

In another embodiment, the present invention provides a method for enhancing oncolytic adenovirus replication in prostate cancer cells or cancer cells. The method includes introducing a nucleic acid sequence encoding an shRNA in the E1 region or the Fiber region of the oncolytic adenovirus, and contacting the prostate cancer cells or cancer cells with a composition including the oncolytic adenovirus. In one aspect, the shRNA is targeted to RNA interference against p21/Waf-1. In another aspect, the oncolytic adenovirus comprises a nucleic acid sequence encoding a tissue specific promoter or a tissue specific enhancer. In various aspects, the tissue specific promoter or tissue specific enhancer is for any tissue of prostate, bladder, liver, kidneys, lungs, breast, retina, brain, ovaries or a combination thereof. In another aspect, the tissue specific promoter is a prostate specific promoter. In another aspect, the tissue specific enhancer is a prostate specific enhancer. In another aspect, the composition includes a therapeutically effective amount of the oncolytic adenovirus. In another aspect, the composition includes at least one pharmaceutically acceptable carrier. In another aspect, the composition includes a non-adenovirus agent for the treatment of cancer. In an additional aspect, the non-adenovirus agent includes a chemotherapeutic agent. In another aspect, the non-adenovirus agent includes an antibody or an active fragment thereof. In another aspect, the prostate cancer cells or cancer cells are exposed to a radiation treatment concurrently or separately with the oncolytic adenovirus. In an additional aspect, the radiation treatment is less than 1 Gy. In another aspect, the radiation treatment is less than 5 Gy. In another aspect, the radiation treatment is between 1 Gy and 5 Gy. In another aspect, the radiation treatment is greater than 10 Gy. In another aspect, the radiation treatment is greater than 15 Gy.

In another embodiment, the invention provides a method for enhancing therapeutic efficacy of an oncolytic adenovirus. The method includes introducing a nucleic acid sequence encoding an shRNA in the E1 region or the Fiber region. In one aspect, the shRNA is targeted to RNA interference against p21/Waf-1. In another aspect, the introducing step comprises a recombination event. In another aspect, the oncolytic adenovirus comprises a nucleic acid sequence encoding a tissue specific promoter or a tissue specific enhancer. In various aspects, the tissue specific promoter or tissue specific enhancer is for any tissue of prostate, bladder, liver, kidneys, lungs, breast, retina, brain, ovaries or a combination thereof. In another aspect, the tissue specific promoter is a prostate specific promoter. In another aspect, the tissue specific enhancer is a prostate specific enhancer.

In another embodiment, the invention provides a method for down-regulating p21/Waf-1 in prostate cancer cells or cancer cells. The method includes contacting the prostate cancer cells or cancer cells with a composition including an oncolytic adenovirus. In one aspect, the oncolytic adenovirus comprises an shRNA in the E1 region or the Fiber region and the shRNA is targeted to RNA interference against p21/Waf-1. In another aspect, the oncolytic adenovirus comprises a nucleic acid sequence encoding a tissue specific promoter or a tissue specific enhancer. In various aspects, the tissue specific promoter or tissue specific enhancer is for any tissue of prostate, bladder, liver, kidneys, lungs, breast, retina, brain, ovaries or a combination thereof. In another aspect, the tissue specific promoter is a prostate specific promoter. In another aspect, the tissue specific enhancer is a prostate specific enhancer. In another aspect, the composition includes a therapeutically effective amount of the oncolytic adenovirus. In another aspect, the composition includes at least one pharmaceutically acceptable carrier. In another aspect, the composition includes a non-adenovirus agent for the treatment of cancer. In an additional aspect, the non-adenovirus agent includes a chemotherapeutic agent. In another aspect, the non-adenovirus agent includes an antibody or an active fragment thereof. In another aspect, the prostate cancer cells or cancer cells are exposed to a radiation treatment concurrently or separately with the oncolytic adenovirus. In an additional aspect, the radiation treatment is less than 1 Gy. In another aspect, the radiation treatment is less than 5 Gy. In another aspect, the radiation treatment is between 1 Gy and 5 Gy. In another aspect, the radiation treatment is greater than 10 Gy. In another aspect, the radiation treatment is greater than 15 Gy.

In another embodiment, the present invention also relates to a method for the treatment of a human or animal organism, comprising administering to said organism a therapeutically effective amount of an adenoviral vector of the invention, the polynucleotide or expression vector as described in connection with the use according to the invention, a viral particle or an eukaryotic cell according to the invention.

BRIEF DESCRIPTION OF THE DRAWINGS

FIG. 1 shows that knocking down p21/Waf-1 increases adenovirus titers.

FIG. 3 shows replication kinetics of Ad5-RV004.21 versus Ad5-RV004 in prostate cancer cells. Ad5-RV004.21 or Ad5-RV004 are assessed for kinetics and degree of viral replication by measuring green fluorescent protein (GFP) expression from the major late promoter in the reporter virus FFIG. Since the MLP is only active in late viral replication, this activity is surrogate for viral replication. Ad5-RV004.21 or Ad5-RV004 are used at an equal multiplicity of infection (MOI) of 5 are accessed for kinetics and degree of viral replication by co-infecting with reporter FFIG virus (10 MOI).

FIG. 4 shows down-regulation of p21/Waf-1 by Ad5-RV004.21 in a dose dependent manner.

FIG. 5 shows combinatory studies of Ad5-RV004.21 or Ad5-RV004 with adriamycin.

FIG. 6 shows in vivo oncolytic activity of Ad5-RV004.21 virus. Tumor xenograft model using C4-2 prostate cancer cells are injected at density of $1 \times 10^6$ cells into the dorsal rear flank region of the athymic nude mice to examine the efficacy of Ad5-RV004 or Ad5-RV004.21 viruses. Equal number of infectious viruses i.e., $1 \times 10^8$ plaque forming units(pfu)/tumor of either CN702 (wild type), Ad5-RV004.21, Ad5-RV004, Ad5-RV002-F-Luc virus, or mock infection (phosphate-buffered saline) are administered on day 1, 4 and 7 and measured every other day for 38 days.

FIG. 8A shows hexon amplification is performed using same templates to confirm the virus DNA (A)-PCR amplification using set of primers against E1A promoter and E1A gene of adenovirus used to detect any RCA in Ad5-RV004.21 preps. Equal Pfu/ml (10 pfu/ml) of CN702 (wild type virus) and Ad5-RV004.21 are boiled at 94° C. in PCR for 5 minutes. FIG. 8B shows that two microliters from each sample were used to amplify wild type E1A gene together with water to serve as a negative control.

DETAILED DESCRIPTION OF THE INVENTION

Figure 1A:
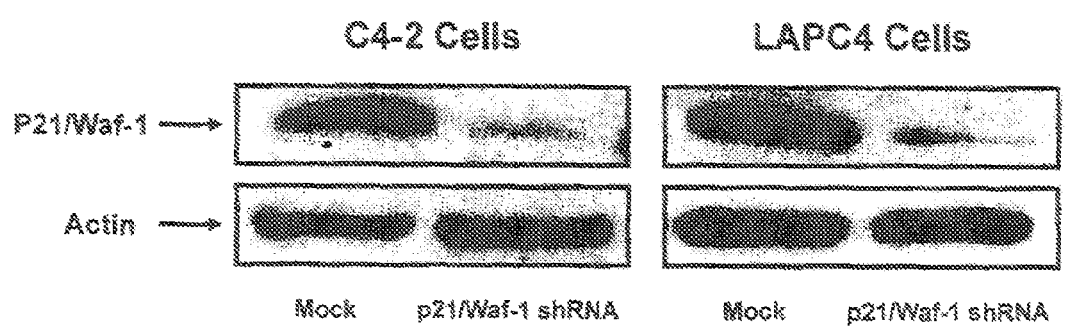
FIG. 1A shows a Western blot analysis for stable knockdown of p21/Waf-1 in C4-2 and LAPC-4 cells using shRNA against p21/Waf-1.

As used herein, the term "vector" refers to a polynucleotide construct designed for transduction/transfection of one or more cell types. Vectors may be, for example, "cloning vectors" which are designed for isolation, propagation and replication of inserted nucleotides, "expression vectors" which are designed for expression of a nucleotide sequence in a host cell, or a "viral vector" which is designed to result in the production of a recombinant virus or virus-like particle, or "shuttle vectors," which comprise the attributes of more than one type of vector.

The term "polynucleotide" or "nucleic acid" refers to a polymeric form of nucleotides of any length, either ribonucleotides and/or deoxyribonucleotides. These terms include a single-, double- or triple-stranded DNA, genomic DNA, cDNA, RNA, DNA-RNA hybrid, or a polymer comprising purine and pyrimidine bases, or other natural, chemically, biochemically modified, non-natural or derivatized nucleotide bases. The backbone of the polynucleotide can comprise sugars and phosphate groups (as may typically be found in RNA or DNA), or modified or substituted sugar or phosphate groups. Alternatively, the backbone of the polynucleotide can comprise a polymer of synthetic subunits such as phosphoramidates and thus can be an oligodeoxynucleoside phosphoramidate (P-NH$_2$) or a mixed phosphoramidate-phosphodiester oligomer. In addition, a double-stranded polynucleotide can be obtained from the single stranded polynucleotide product of chemical synthesis either by synthesizing the complementary strand and annealing the strands under appropriate conditions, or by synthesizing the complementary strand de novo using a DNA polymerase with an appropriate primer.

The following are non-limiting examples of polynucleotides: a gene or gene fragment, exons, introns, mRNA, tRNA, rRNA, ribozymes, cDNA, recombinant polynucleotides, branched polynucleotides, plasmids, vectors, isolated DNA of any sequence, isolated RNA of any sequence, nucleic acid probes, and primers. A polynucleotide may comprise modified nucleotides, such as methylated nucleotides and nucleotide analogs, uracyl, other sugars and linking groups such as fluororibose and thioate, and nucleotide branches. The sequence of nucleotides may be interrupted by non-nucleotide components. A polynucleotide may be further modified after polymerization, such as by conjugation with a labeling component. Other types of modifications included in this definition are caps, substitution of one or more of the naturally occurring nucleotides with an analog, and introduction of means for attaching the polynucleotide to proteins, metal ions, labeling components, other polynucleotides, or a solid support.

The term "plasmid" refers to an extrachromosomal circular DNA capable of autonomous replication in a given cell. The range of suitable plasmids is very large. Preferably, the plasmid is designed for amplification in bacteria and for expression in a eukaryotic target cell. Such plasmids can be purchased from a variety of manufacturers. Exemplary plasmids include but are not limited to those derived from pBR322 (Gibco BRL), pUC (Gibco BRL), pBluescript (Stratagene), pREP4, pCEP4 (Invitrogene), pCI (Promega) and p Poly (Lathe et al., Gene 57 (1987), 193-201). Plasmids can also be engineered by standard molecular biology techniques (Sambrook et al., Laboratory Manual, Cold Spring Harbor Laboratory Press, Cold Spring Harbor (1989), N.Y.). It may also comprise a selection gene in order to select or to identify the transfected cells (e.g., by complementation of a cell auxotrophy or by antibiotic resistance), stabilizing elements (e.g., cer sequence) or integrative elements (e.g., LTR viral sequences and transposons).

The term "shuttle plasmid" refers to a plasmid comprising a unique restriction site between certain homologous recombination sites and used to insert a desired nucleic acid molecule, i.e., a nucleic acid molecule encoding a desired product, into a recombinant adenoviral vector. The homologous recombination sites can be, for example, Ad5 right and Ad5 left. In further embodiments, the shuttle plasmid may have a tissue specific promoter which controls the expression of the desired nucleic acid molecule. The shuttle plasmid also contains a majority of the viral genes necessary to form viral particles. However, the shuttle plasmid does not contain all necessary genes to form viral particles.

The term "promoter" refers to the DNA region, usually upstream to the coding sequence of a gene or operon, which binds RNA polymerase and directs the enzyme to the correct transcriptional start site.

The term "enhancer" refers to a sequence found in eukaryotes and certain eukaryotic viruses which can increase transcription from a gene when located (in either orientation) up to several kilobases from the gene being studied. These sequences usually act as enhancers when on the 5' side (upstream) of the gene in question. However, some enhancers are active when placed on the 3' side (downstream) of the gene. In some cases, enhancer elements can activate transcription from a gene with no (known) promoter.

The term "replication" means duplication of a vector. This duplication, in the case of viruses, can occur at the level of nucleic acid, or at the level of infectious viral particle. In the case of DNA viruses, replication at the nucleic acid level comprises DNA replication. In the case of RNA viruses, nucleic acid replication comprises replication into plus or minus strand (or both). In the case if retroviruses, replication at the nucleic acid level includes the production of cDNA as well as the further production of RNA viral genomes. The essential feature is the generation of nucleic acid copies of the original viral vector. However, replication also includes the formation of infectious DNA or RNA viral particles. Such particles may successively infect cells in a given target tissue, thus distributing the vector through all or a significant portion of the target tissue.

The term "tissue-specific" is intended to mean that the transcriptional regulatory sequence to which the gene essential for replication is operably linked functions specifically in that tissue so that replication proceeds in that tissue. This can occur by the presence in that tissue, and not in non-target tissues, of positive transcription factors that activate the transcriptional regulatory sequence. It can also occur by the absence of transcription inhibiting factors that normally occur in non-target tissues and prevent transcription as a result of the transcription regulatory sequence. Thus, when transcription occurs, it proceeds into the gene essential for replication such that in that target tissue, replication of the vector and its attendant functions occur.

As described herein, tissue specificity is particularly relevant in the treatment of the abnormal counterpart of a normal tissue. Such counterparts include, but are not limited to, cancerous prostate tissue and normal prostate tissue. Tissue specificity also includes the presence of an abnormal tissue type interspersed with normal tissue of a different tissue type, as for example in the case of metastases of prostate cancer, and the like, into tissue such as liver. In this case, the target tissue is the abnormal tissue, and tissue specificity reflects the restriction of vector replication to the abnormal tissue interspersed in the normal tissue. It is also to be understood that tissue specificity, in the context of treatment, is particularly relevant in vivo. However, as described herein, ex vivo treatment and tissue replacement also falls within the concept of tissue specificity according to the present invention.

The term "Androgen Receptor" or AR refers to a protein whose function is to specifically bind to androgen and, as a consequence of the specific binding, recognize and bind to an androgen response element (ARE), following which the AR is capable of regulating transcriptional activity. The AR is a nuclear receptor that, when activated, binds to cellular androgen-responsive element(s). In normal cells the AR is activated by androgen, but in non-normal cells (including malignant cells) the AR may be activated by non-androgenic agents, including hormones other than androgens. Encompassed in the term "Androgen Receptor" are mutant forms of an androgen receptor, such as those characterized by amino acid additions, insertions, truncations and deletions, as long as the function is sufficiently preserved. Mutants include androgen receptors with amino acid additions, insertions, truncations and deletions, as long as the function is sufficiently preserved. In this context, a functional androgen receptor is one that binds both androgen and, upon androgen binding, an ARE.

A "therapeutically effective amount" refers to an amount at least partially effective, at dosages and for periods of time necessary, to achieve the desired therapeutic result to thereby influence the therapeutic course of a particular disease state. A therapeutically effective amount of an active agent may vary according to factors such as the disease state, age, sex, and weight of the individual, and the ability of the agent to elicit a desired response in the individual. Dosage regimens may be adjusted to provide the optimum therapeutic response. A therapeutically effective amount is also one in which any toxic or detrimental effects of the agent are outweighed by the therapeutically beneficial effects. A "therapeutically effective amount" is an amount sufficient to at least partially affect beneficial or desired results, including clinical results. An effective amount can be administered in one or more administrations. For purposes of this invention, an effective amount of an adenoviral vector is an amount that is sufficient to at least partially palliate, ameliorate, stabilize, reverse, slow or delay the progression of the disease state.

In another embodiment, the active agent is formulated in the composition in a prophylactically effective amount. A "prophylactically effective amount" refers to an amount effective, at dosages and for periods of time necessary, to achieve the desired prophylactic result. Typically, since a prophylactic dose is used in subjects prior to or at an earlier stage of disease, the prophylactically effective amount will be less than the therapeutically effective amount.

As used herein, "treatment" of a subject includes the application or administration of a therapeutic agent to a subject, or application or administration of a therapeutic agent to a cell or tissue from a subject, who has a diseases or disorder (e.g., cancer), has a symptom of a disease or disorder, or is at risk of (or susceptible to) a disease or disorder, with the purpose of curing, healing, alleviating, relieving, altering, remedying, ameliorating, improving, or affecting the disease or disorder, the symptom of the disease or disorder, or the risk of (or susceptibility to) the disease or disorder.

As used herein, "suppressing tumor growth" refers to at least partially reducing the rate of growth of a tumor, halting tumor growth completely, causing a regression in the size of an existing tumor, eradicating an existing tumor and/or preventing the occurrence of additional tumors upon treatment with the compositions, kits or methods of the present invention. "Suppressing" tumor growth indicates a growth state that is curtailed when compared to growth by cells treated only with a DNA-damaging agent (e.g., radiation or chemotherapy), without treatment with the siRNA of the invention. Tumor cell growth can be assessed by any means known in the art, including, but not limited to, directly measuring tumor size, radiographic imaging, utilizing serum biomarkers of disease burden (e.g., serum PSA), determining whether tumor cells are proliferating using a $^3$H-thymidine incorporation assay or clonogenic assay, or counting tumor cells.

As used herein, "pharmaceutically acceptable carrier" includes any and all solvents, dispersion media, coatings, antibacterial and antifungal agents, isotonic and absorption delaying agents, and the like that are physiologically compatible. The type of carrier can be selected based upon the intended route of administration. In various embodiments, the carrier is suitable for intravenous, intraperitoneal, subcutaneous, intramuscular, topical, transdermal or oral administration. Pharmaceutically acceptable carriers include sterile aqueous solutions or dispersions and sterile powders for the extemporaneous preparation of sterile injectable solutions or dispersion. The use of such media and agents for pharmaceutically active substances is well known in the art. Except insofar as any conventional media or agent is incompatible with the active compound, use thereof in the pharmaceutical compositions of the invention is contemplated. Supplementary active compounds can also be incorporated into the compositions.

Therapeutic compositions typically must be sterile and stable under the conditions of manufacture and storage. The composition can be formulated as a solution, microemulsion, liposome, or other ordered structure suitable to high drug concentration. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. In many cases, it will be preferable to include isotonic agents, for example, sugars, polyalcohols such as mannitol, sorbitol, or sodium chloride in the composition. Prolonged absorption of the injectable compositions can be brought about by including in the composition an agent which delays absorption, for example, monostearate salts and gelatin. Moreover, the composition can be administered in a time release formulation, for example in a composition which includes a slow release polymer. The composition can be prepared with carriers that will protect the oncolytic adenovirus or other agents against rapid release, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, polylactic acid and polylactic, polyglycolic copolymers (PLG). Many methods for the preparation of such formulations are generally known to those skilled in the art.

Sterile injectable solutions can be prepared by incorporating the composition in the required amount in an appropriate solvent with one or a combination of ingredients as required, followed by filtered sterilization. Generally, dispersions are prepared by incorporating the active compound into a sterile vehicle which contains a basic dispersion medium and the required ingredients. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

As used herein, "adenovirus" refers to the virus itself or derivatives thereof. The term covers all serotypes and subtypes and both naturally occurring and recombinant forms, except where otherwise indicated. Thus, the term "adenovirus" or "adenoviral particle" is used to include any and all viruses that can be categorized as an adenovirus, including any adenovirus that infects a human or an animal, including all groups, subgroups, and serotypes. There are at least 51 serotypes of adenovirus that classified into several subgroups. For example, subgroup A includes adenovirus serotypes 12, 18, and 31. Subgroup C includes adenovirus serotypes 1, 2, 5, and 6. Subgroup D includes adenovirus serotype 8, 9, 10, 13, 15, 17, 19, 20, 22-30, 32, 33, 36-39, and 42-49. Subgroup E includes adenovirus serotype 4. Subgroup F includes adenovirus serotypes 40 and 41. These latter two serotypes have a long and a short Fiber protein. Thus, as used herein an "adenovirus" or "adenovirus particle" may include a packaged vector or genome. Depending upon the context reference to, "adenovirus" can also include adenoviral vectors.

An "adenovirus vector," "adenoviral vector," or "adenovirus construct" is a term well understood in the art and generally comprises a polynucleotide comprising all or a portion of an adenovirus genome. Thus, an "adenovirus vector," "adenoviral vector," or "adenovirus construct" refers to any of several forms, including, but not limited to, DNA, DNA encapsulated in an adenovirus coat, DNA packaged in another viral or viral-like form (such as herpes simplex, and AAV), DNA encapsulated in liposomes, DNA complexed with polylysine, complexed with synthetic polycationic molecules, conjugated with transferrin, and complexed with compounds such as PEG to immunologically "mask" the molecule and/or increase half-life, and conjugated to a non-viral protein. Preferably, the polynucleotide is DNA.

The adenoviral vector typically contains most of the adenoviral genome. The adenoviral vector may also contain a bacterial origin of replication. Portions of the wild-type adenoviral genome may be deleted to permit insertion of desired products and the packaging of recombinant adenoviral vectors containing the desired genes.

As used herein, "DNA" includes not only bases A, T, C, and G, but also includes any of their analogs or modified forms of these bases, such as methylated nucleotides, internucleotide modifications such as uncharged linkages and thioates, use of sugar analogs, and modified and/or alternative backbone structures, such as polyamides. For purposes of this invention, adenovirus vectors are replication-competent in a target cell.

Recombinant adenoviruses are currently used for a variety of purposes, including gene transfer in vitro, vaccination in vivo, and gene therapy. Several features of adenovirus biology have made such viruses the vectors of choice for certain of these applications. For example, adenoviruses transfer genes to a broad spectrum of cell types, and gene transfer is not dependent on active cell division. Additionally, high titers of virus and high levels of transgene expression can generally be obtained.

Decades of study of adenovirus biology have resulted in a detailed picture of the viral life cycle and the functions of the majority of viral proteins. The genome of the most commonly used human adenovirus (serotype 5) consists of a linear, 36 kb, double-stranded DNA molecule. Both strands are transcribed and nearly all transcripts are heavily spliced. Viral transcription units are conventionally referred to as early (E1, E2, E3 and E4) and late, depending on their temporal expression relative to the onset of viral DNA replication. The high density and complexity of the viral transcription units poses problems for recombinant manipulation, which is therefore usually restricted to specific regions, particularly E1, E2A, E3, and E4. In most recombinant vectors, transgenes are introduced in place of E1 or E3, the former supplied exogenously. The E1 deletion renders the viruses defective for replication and incapable of producing infectious viral particles in target cells; the E3 region encodes proteins involved in evading host immunity, and is dispensable for viral production per se.

Two approaches have traditionally been used to generate recombinant adenoviruses. The first involves direct ligation of DNA fragments of the adenoviral genome to restriction endonuclease fragments containing a transgene. The low efficiency of large fragment ligations and the scarcity of unique restriction sites have made this approach technically challenging. The second and more widely used method involves homologous recombination in mammalian cells capable of complementing defective adenoviruses ("packaging lines"). Homologous recombination results in a defective adenovirus which can replicate in the packaging line (e.g., 293 or 911 cells) which supplies the missing gene products (e.g., E1). The desired recombinants are identified by screening individual plaques generated in a lawn of packaging cells. The low efficiency of homologous recombination, the need for repeated rounds of plaque purification, and the long times required for completion of the viral production process have hampered more widespread use of adenoviral vector technology.

Existing adenoviral vectors and systems have been described in U.S. Pat. No. 7,662,795, and patent application publications US 2005/0245472, US 2009/0042257, and US 2009/0074658, the contents of which are incorporated herein by reference in their entireties.

Conditionally replicating adenoviruses (CRAds) represent a promising modality for the treatment of neoplastic diseases, including prostate cancer. The present invention provides the importance of cyclin dependent kinases inhibitor p21/Waf-1, on viral replication and tumor growth. The present invention provides p21/Waf-1 shRNA on the induction of an ARE based promoter driving the E1A gene. The present invention also provides the use of RNA interference to overcome promoter weaknesses for tissue specific oncolytic viruses, as well as the cellular inhibitor pathways on viral life cycle. Using RNA interference against p21/Waf-1 in the backbone of prostate specific CRAd, the present invention provides an increase in viral replication and viral oncolysis of prostate cancer cells both in vitro and in vivo. Taken together this unique approach of using RNA interference to modulate cellular inhibitory pathways as well as to induce tissue specific promoters driving viral replication genes has significant implications in the development of prostate-specific CRAd therapies.

The cell-cycle-dependent kinase inhibitor, p21/Waf-1, has been linked to many cellular functions. For example, it is also known to interact with proliferating cell nuclear antigen (PCNA), which can inversely affect DNA repair and replication. Similarly, p21/Waf-1 is found to interact with pro-caspase-3 in mitochondria, which regulates caspase-3 activation and apoptotic cell death. It is also a direct downstream target of the tumor suppressor p53. Elevated level of p21/Waf-1 is known to arrest cells in both G1 and G2 phases of the cell cycle by inhibiting cyclin-dependent kinase (CDK) complexes.

In one embodiment, the present invention provides a CRAd which selectively replicates in prostate cells via prostate specific rat probasin (PBN) promoter/driving E1A, with enhanced therapeutic effect due to constitutive expression of an anti-p21/Waf-1 shRNA located in the Fiber-gene region. In one embodiment, the present invention provides the use of shRNA to enhance the natural viral lifecycle for use in gene therapy. Knocking down p21/Waf-1 not only can help in virus replication but also can enhance the induction of prostate specific ARE based promoter that controls E1A expression. Taken together, the present invention provides the feasibility of developing enhanced oncolytic viral gene therapies with shRNAs to modulate cellular pathways that attenuate viral replication.

The present invention provides the use of an anti-p21/Waf-1 shRNA incorporated into the backbone of a prostate specific CRAd to augment its natural life cycle. The approach enables the p21/Waf1 knockdown to result in augmented viral replication in general but also specifically to upregulate the Androgen Receptor, as a consequence of the prostate specific promoter/enhancer constructs driving E1A. Therefore, the prostate specific CRAd is markedly increased in its activity against prostate cancer cells The present invention also provides the use of RNAi to induce promoter activity to enhance the therapeutic efficacy of a CRAd virus as well as to augment viral life cycle.

In one embodiment, the present invention provides that prostate cancer cells with knockdown p21/Waf-1 phenotypes tend to have more AR expression and AR dependent promoter activity compared to controls. Using an shRNA against p21/Waf-1 in the viral backbone, the present invention provides accelerated viral replication and enhanced viral cytotoxicity against prostate cancer cells.

RNA interference (RNAi) was first noted in *Caenorhabditis elegans* and plants as a novel mechanism of post-transcriptional gene silencing and has since been discovered in many eukaryotes. Rapid progress has been made in the use of RNAi and more specifically siRNAs as a means of attenuating the expression of specific proteins both in vitro and in vivo enabling any protein target, where the cDNA sequence is known, to be inhibited by these sequence-specific, double-stranded RNA molecules.

RNA interference (RNAi) is an evolutionarily conserved sequence-specific post-transcriptional gene silencing mechanism and is thought to function in part as an innate intracellular antiviral immune response. In one embodiment, the present invention provides prostate specific CRAds using the Fiber region, Cre-recombinase based, pFex system where the shRNA against p21/Waf-1 is placed downstream of the Fiber gene. The CRAd is rendered prostate specific by placing the E1A gene under the control of the PSA enhancer fused to the rat probasin promoter. Using the FFIG reporter assay, real-time enhanced replication of the Ad5-RV004.21 in different prostate cancer cell lines can be obtained. This phenomenon is attributed to p21/Waf-1 knockdown because a similar virus lacking the shRNA against p21/Waf-1 is unable to show as efficient replication or as high viral titers in prostate cancer cells (FIG. 3). The present invention further provides utility in an in vivo model. Animal xenografts are injected with the same dose ($3 \times 10^8$ PFU) of Ad5-RV004.21 or CN702 (E3 deleted wild type virus) and show no significant difference in tumor regression at any given time point throughout the course of study. However, Ad5-RV004 (no shRNA) treatment is less effective in suppressing tumor growth when compared to either wild type CN702 or Ad5-RV004.21 treatments (FIG. 5). Other contributing factors in the observation that Ad5-RV004 is attenuated compared to Ad5-RV004.21 can be due to the tumor microenvironment which is significantly different from that of normal tissues. A major difference is seen in the disorganized vasculature of tumors, which results in an unbalanced blood supply and significant perfusion heterogeneities.

Many regions within tumors are transiently or chronically hypoxic. It has been previously reported that hypoxic conditions lead to cell cycle arrest through p21/Waf-1 over expression and induction of apoptosis that is independent of p53. The present invention provides that any processes that results in over-expression of p21/Waf-1 can be counter-productive in current oncolytic adenoviral therapy. An additional benefit in employing p21/Waf-1 knockdown in prostate cancer cells is a desire to enhance bio-sensitization of our CRAd vectors to conventional chemotherapeutic agents. The present invention provides that treating p21/Waf-1 knockdown C4-2 cells with either adriamycin or HDACI can show an increase in cell death compared to the wild type cell lines. This finding can be further confirmed when CRAd viruses are engineered to express shRNA against the p21/Waf-1. A super-additive (synergistic) effect is observed at any given time point during the course of the experiment only in combinatory studies using adriamycin and Ad5-RV004.21 (see FIG. 5B) further strengthening the importance of p21/Waf-1 shRNA in adenoviral based bio-sensitization of drug targeted therapies. Other utilities of this approach could be in combination with radiation therapies as it has been reported that over expression of p21/Waf-1 leads to the protective cellular mechanism during radiation therapies.

Since the present invention provides the use of a p21/Waf-1 shRNA incorporated into the backbone of a prostate specific CRAd to augment its natural life cycle and the use to induce promoters containing AREs which drive the viral replication genes, the present invention also provides the use of RNAi to induce promoter activity enhancing the therapeutic efficacy of a CRAd. The idea to shorten the viral life cycle using shRNAs by targeting cellular inhibitory pathways as well as inducing tissue specific promoters driving viral gene for robust viral replication and at the same time maintaining tissue specificity can be very well translated to different tissue types including but not limited to prostate, bladder, liver, kidneys, lungs, breast, retina, brain, ovaries etc and to all other gene therapy viral vectors. Similarly microRNAs can also be utilized in the same ways to induce viral life cycle inside the cancer cell.

Delivery of adenoviral vectors can be accomplished by either site-specific injection (local administration) or intravenously (systemic administration). Site-specific injections of adenoviral vectors may include, for example, injections into the portal vein of the liver as well as intraperitoneal, intra-pleural, intrathecal, intra-arterial, intra-tumor injections or topical application. These methods are easily accommodated in treatments using adenoviral vectors.

The adenoviral vectors may be delivered to the target cell in a variety of ways, including, but not limited to, liposomes, general transfection methods that are well known in the art (such as calcium phosphate precipitation or electroporation), direct injection, and intravenous infusion. The means of delivery will depend in large part on the particular adenoviral vector (including its form) as well as the type and location of the target cells (i.e., whether the cells are to be transfected or transformed in vitro or in vivo). If used as a packaged adenovirus, adenovirus vectors may be administered in an appropriate physiologically acceptable carrier at a dose of about 1 to about 10. The multiplicity of infection will generally be in the range of about 0.001 to 100. If administered as a polynucleotide construct (i.e., not packaged as a virus) about 0.01 µg to about 1000 µg of an adenoviral vector can be administered. The adenoviral vector(s) may be administered one or more times, depending upon the intended use and the immune response potential of the host, and may also be administered as multiple, simultaneous injections. If an immune response is undesirable, the immune response may be diminished by employing a variety of immunosuppressants, so as to permit repetitive administration, without a strong immune response. If packaged as another viral form, such as HSV, an amount to be administered is based on standard knowledge about that particular virus (which is readily obtainable from, for example, published literature) and can be determined empirically.

Thus, the adenoviral vector, the polynucleotide and expression vector or the viral particle of the present invention may be delivered in vivo to the human or animal organism by specific delivery means adapted to the pathology to be treated. For example, a balloon catheter or a stent coated with the adenoviral vector, the expression vector carrying the polynucleotide or the viral particle may be employed to efficiently reach the cardiovascular system. It is also possible to deliver said therapeutic agents by direct administration, e.g., intravenously, in an accessible tumor, in the lungs by aerosolization, and the like. Alternatively, one may employ eukaryotic host cells that have been engineered ex vivo to contain the adenoviral vector, the expression vector carrying the polynucleotide or the viral particle according to the invention. Methods for introducing such elements into an eukaryotic cell are well known to those skilled in the art and include microinjection of minute amounts of DNA into the nucleus of a cell, transfection with calcium phosphate, electroporation, lipofection/liposome fusion, and particle bombardment.

Administration of the above-described methods may also include repeat doses or courses of target-cell specific adenovirus depending, inter alia, upon the individual's response and the characteristics of the individual's disease. Repeat doses may be undertaken immediately following the first course of treatment (i.e., within one day), or after an interval of days, weeks or months to achieve and/or maintain suppression of tumor growth.

Generally, an effective amount of adenovirus vector is administered, i.e., amounts sufficient to achieve the desired result, based on general empirical knowledge of a population's response to such amounts. Some individuals are refractory to these treatments, and it is understood that the methods encompass administration to these individuals. The amount to be given depends, inter alia, on the stage of the cancer, the condition of the individual, the extent of disease, the route of administration, how many doses will be administered, and the desired objective.

The methods of the present invention can be applied to the treatment of prostate cancer in male subjects at any stage of the cancer, although certain treatment methods are more preferred for particular cancer stages. Prostate cancer is commonly evaluated according to a scale divided into four lettered stages: A, B, C and D. Tumors in stage A are microscopic; stage A1 designates tumors confined to a relatively small area and composed of well-differentiated tissue, while stage A2 tumors are more diffuse and less well differentiated. Stage B tumors are large enough to be felt during a rectal examination, while stage C prostate cancers have spread throughout the gland and typically have pushed past the borders of the prostate into surrounding structures. Stage D tumors have metastasized, e.g., to lymph nodes, bone, or other organs. Alternatively, tumors can be staged by the TNM staging system, in which tumors are ranked on a scale of progressively worsening disease from T1 a to T4b (e.g., T1c tumors are non-palpable and non-visible that were detected by elevated blood levels of prostate specific antigen). The methods of the invention are useful in the treatment of any stage of prostate cancer. However, it will be appreciated by the skilled artisan that methods involving procedures for removal or destruction of prostatic tumor tissue preferably are employed with non-metastasized cancers. For example, radical prostatectomy preferably is used with stage A, B and some stage C tumors (i.e., where the tumor growth has not extended considerably beyond the borders of the prostate gland) as well as stage T1 c tumors. Radiation therapy (e.g., external or interstitial) preferably is used with stage A, B or C tumors as well as T1c tumors.

To assess the efficacy of a treatment method of the invention, the size of the prostate can be determined by methods known in the art, for example, rectal examination, transrectal ultrasonography or magnetic resonance imaging (MRI). Moreover, the size or extent of the prostate tumor (and metastatic tumors, if any) can be assessed by known methods including a prostate-specific antigen blood test, bone scanning, X-rays, skeletal survey, intravenous pyelography, CAT-scan, MRI, physical examination, biopsy, and the like. For treatment methods that involve surgery (e.g., in neoadjuvant therapy wherein a peptide compound is administered prior to a radical prostatectomy), the tumor can also be staged during surgery (e.g., the prostate gland can be examined during surgery and/or a biopsy can be taken and examined). Thus, clinical staging and/or surgical staging may be used to evaluate the extent of disease.

A preferred method of evaluating the extent of prostate cancer is to assay the level of prostate-specific antigen (PSA) in a subject's blood. The PSA blood test is a reasonably specific, sensitive, rapid, and inexpensive tool for screening for prostate cancer. In general, a blood PSA level above 4 ng/ml is considered to be suggestive of the presence of prostate cancer, with levels above 10 ng/ml being particularly indicative of cancer. For a subject undergoing treatment with a peptide compound according to the methods of the invention, a pretreatment level of PSA can be established and the efficacy of the treatment assessed by monitoring periodically the PSA level in the subject's blood, wherein decreased PSA levels are used as an indicator of the efficacy of the treatment. The PSA nadir (i.e., the point at which PSA levels do not decrease further even upon further treatment with a peptide compound) can be used as the indicator point for initiation of a second therapy, for example for performance of a procedure that removes or destroys prostatic tumor tissue (including radical prostatectomy, cryosurgery and/or radiation therapy). It is expected that the PSA nadir will be reached sooner using a peptide compound, as compared to treatments which do not include using a peptide compound.

Additionally or alternatively, plasma concentrations of sex hormones can be monitored to assess the efficacy of the drug therapy. Concentrations of hormones such as testosterone, dihydrotestosterone, dehydroepiandrosterone (DHEA), DHEA-sulfate, androst-5-ene-3β, 17-diol, and the estrogen 17β-estradiol can all be measured by methods known the skilled artisan. Preferably, decreased levels of testosterone and dihydrotestosterone can be used as indicators of treatment efficacy.

In another embodiment, the methods of the invention can be administered in conjunction with other known treatments for cancer, including, but not limited to, mechanical removal of cancerous cells (e.g., surgical removal of a tumor), and administration of chemotherapeutic agents. There are many known chemotherapeutic agents used to treat cancer which act to kill cancer cells and/or slow their growth through other mechanisms. The administrations of such additional treatments and/or agents are intended to be included in the methods of the present invention.

For example, examples of chemotherapeutic agents that may be used in conjunction with the methods of the invention include, but are not limited to, antimetabolites such as folate analogs (e.g., methotrexate), purine analogs (e.g., fludarabine, mercaptopurine, and thioguanine (e.g., 6-TG)), adenosine analogs (e.g., cladribine, and pentostatin), pyrimidine analogs (e.g., capecitabine, cytarabine, depocyt, floxuridine, fluorouracil (e.g., 5-FU); and gemcitabine), and substituted ureas (e.g., hydroxyurea); natural products such as antitumor antibiotics (e.g., bleomycin, dactinomycin, actinomycin D, daunorubicin, daunomycin, DaunoXome (liposomal daunorubicin), doxorubicin, Doxil (liposomal-doxorubicin), epirubicin, idarubicin, mitoxantrone, and mitomycin C), epipodophyllotoxins (e.g., etoposide and teniposide), microtuble agents (e.g., docetaxel, paclitaxel, vinblastine, vincristine, and vinorelbine), camptothecin analogs (e.g., irinotecan and topotecan), enzymes (e.g., asparaginase), and monoclonal antibodies (e.g., alemtuzamab, gemtuzumab ozogamicin, ibritumomab tiuxetan, nofetumomab, rituximab, tositumomab, and trastuzumab). Those skilled in the art will recognize that any of these chemotherapeutic agents and others can be used in combination with the oncolytic adenovirus of the invention.

One aspect of the invention relates to a method for treating prostate cancer in a subject in need of such treatment, comprising administering to the subject a adenoviral particle of the invention, and performing on the subject at least one procedure that removes or destroys prostatic tumor tissue, such as a radical prostatectomy, cryosurgery, external radiation therapy (e.g., X-ray therapy) or interstitial radiation therapy (e.g., implantation of a radioactive seed). The adenoviral particle may be administered to the subject prior to or subsequent to performing the procedure that removes or destroys pro static tumor tissue. In one such embodiment, administration of an adenoviral particle is preferably for a period sufficient to cause the prostate or prostatic tumor tissue to shrink in size prior to performing the procedure that removes or destroys prostatic tumor tissue. A suitable period for preadministration of an adenoviral particle typically is between about one day and about one year, more preferably between about three days and about six months.

In certain situations, it may be desirable to use an antiandrogen, and thus in another embodiment, this treatment method can further involve administering an antiandrogen to the subject in combination with the adenoviral particle. In yet another embodiment, this treatment method can further involve administering one or more inhibitors of sex steroid biosynthesis to the subject in combination with the peptide compound (optionally in further combination with an antiandrogen) prior to or subsequent to performing the procedure that removes or destroys prostatic tumor tissue.

In another embodiment, the adenoviral particle of the present invention may be administered in conjunction with an LHRH agonist, as described in U.S. Pat. Nos. 5,843,902, 5,780,435, and 6,153,586, the contents of which are incorporated herein by reference in their entireties, or an LH receptor antagonist.

Those of skill in the art will recognize that while it may not be necessary to combine adenoviral particle therapy with additional drugs or treatments, in certain situation it may be desirable to further combine the compound with other drugs or treatments to achieve the greatest therapeutic effect.

The present invention also encompasses combinations of the oncolytic adenovirus with any of polyclonal and monoclonal human, chimeric, and humanized antibodies directed to the novel tumor-associated antigens, cells, and cell S lines of the invention, including tumor-associated antigen-expressing and tumor associated antigen- and cytokine-expressing autologous and allogeneic tumor and-normal cells. These antibodies can then be used to prepare antibody-containing compositions used in the therapeutic methods of the present invention.

The antibodies can be prepared via techniques well known to those having ordinary skill in the art (see, e.g., Harlow and Lane (eds.) Antibodies, A Laboratory Manual, Cold Spring Harbor Laboratories, 1988). In particular, monoclonal antibodies produced against immortal tumor cell lines according to the present invention are useful in the detection and therapy of various cancers, such as prostate cancer. The antibody or antigen binding portion thereof binds to malignant cells. Thus, the antibody or antigen binding portion thereof is immunoreactive with at least one tumor rejection antigen or with at least one tumor-associated antigen and epitopes thereof.

Exemplary antibody molecules are intact immunoglobulin molecules, substantially intact immunoglobulin molecules or those portions of an immunoglobulin molecule that contain the antigen binding site, including Fab, F(ab)$_2$, and F(v). Polyclonal or monoclonal antibodies may be produced by methods known in the art. The antibodies or active fragments thereof may also be produced by genetic engineering including chimeric antibody, single chain antibody. The antibody or an active fragment thereof may be used as an immunotherapeutic. The antibody or an active fragment thereof may be administered alone, or in combination with chemotherapeutics or immunosuppressive agents as are known in the art.

The antibody or an active fragment thereof may also be used as an immunotoxin to specifically target and kill malignant primary and metastatic cells. Immunotoxins are characterized by two components and are particularly useful for killing selected cells in vitro or in vivo. One component is a cytotoxic agent which is usually fatal to a cell when attached or absorbed. The second component, known as the delivery vehicle, provides a means for delivering the toxic agent to a particular cell type, such a malignant prostate cells. The two components are commonly bonded together by any of a variety of well-known chemical procedures. For example, when the cytotoxic agent is a protein, the linkage to the antibody may be by way of hetero bifunctional crosslinkers, e.g., SPDP, carbodiimide, glutaraldehyde, and the like. Production of various immunotoxins is well-known in the art.

A variety of cytotoxic agents are suitable for use in immunotoxins. Cytotoxic agents include, but are not limited to, radionuclides, such as Iodine$^{131}$ or other isotopes of iodine, Yttrium$^{90}$, Thenium$^{188}$, and Bismuth or other alpha emitters; a number of chemotherapeutic drugs, such as vindesine, methotrexate, andriamycin, taxol, and ciplatinum; and cytotoxic proteins such as ribosomal inhibiting proteins like *Pseudomonas* exotoxin A, ricin, diphtheria toxin, ricin A chain and the like.

It is to be understood that the embodiments of the invention herein described are merely illustrative of the application of the principles of the invention. Reference herein to details of the illustrated embodiments is not intended to limit the scope of the claims, which themselves recite those features regarded as essential to the invention. The following examples are intended to illustrate but not limit the invention.

EXAMPLE 1

Reporter Based Quantification of Viral Replication

Reagents and Antibodies: For Western blot analysis the following antibodies can be used: mAb-p21/Waf-1 (1:1000, Upstate Charlottesville, Va.), mAb-AR (1:1000, Santa Crutz Biotech USA), mAb-beta Actin (1:25,000) and Anti-mouse IgG HRP-conjugated (1:20,000 Sigma Aldrich, USA). All restriction enzymes can be purchased from New England Biolabs (Beverly, Mass.). Cell culture Media can be obtained from Cellgro (Herndon, Va.). Trypan blue can be purchased from Invitrogen (Carlsbad, Calif.). The majority of all other chemical reagents and compounds can be ordered from Sigma, unless otherwise specified.

Cell Culture and Generation of Stable Cells Lines: LNCaP and HEK293 cell lines can be purchased from American Tissue Culture Collection (Manassas, Va.). LAPC4 and C4-2 cell are obtained from Dr. John Iscaas (Johns Hopkins University). LNCaP, LAPC4, C4-2 and HEK293 cells are maintained in RPMI1640 medium with L-Glutamine (Cellgro, Herndon, Va.) and DMEM respectively Cellgro, Herndon, Va.) and supplemented with heat inactivated fetal bovine serum 10% (GIBCO, Carlsbad, Calif.), Ciprofloxacin Hydrochloride 5 µg/ml (US Biological, Swampscott, Mass.), and Gentamicin 50 µg/ml (Quality Biological Inc., Gaithersburg, Md.). Cells are allowed to grow until 80-90% confluency and harvested with 0.05% trypsin/0.5 mM EDTA (Cellgro, Herndon, Va.) before each subsequent passage. Stable p21/Waf-1 knockdown C4-2 and LAPC4 cells or control cells are generated by transfection of plasmids. Briefly, cells are seeded into six-well plates at approximately 60 to 70% confluence 12 to 24 hours prior to transfections. Plasmid DNA, pSuper-Puro-GFP or pSuper-Puro-GPF shRNA p21/Waf-1 is used to transfect the C4-2 and LAPC-4 cells using Lipofectamine 2000 reagent (Life Technologies) according to the manufacturer's instructions. Cell monolayers are trypsinized 24 hours after transfection and transferred into T25 flasks or 100-mm-diameter culture dishes. Cells are than selected by growth in complete medium containing 2 µg/ml of puromycin for 4 weeks. Viable clones are pooled together and cultured for expansion in T75 Flasks and at the same time assayed by western blot to ensure p21/Waf-1 knockdowns.

Western Blot Analysis: Cells are washed with 1×PBS and re-suspended with 5 volumes of cold lysis buffer (50 mM Tris-HCl, pH 7.5, 250 mM NaCl, 5 mM EDTA, 50 mM NaF, 0.5% NP-40) supplemented with protease inhibitor cocktail (Roche, Indianapolis, Ind.). The cell lysate is incubated on ice for 30 min and then centrifuged for 10 minutes at 4° C. Equal amounts of proteins are separated by SDS-PAGE, and the resolved proteins are then transferred to a nitrocellulose membrane. After blocking with 5% nonfat milk in TBST overnight at 4° C., the blot is incubated with primary antibody for one hour at room temperature. The membrane is then probed with HRP-conjugated secondary antibody for one hour and developed (ECL-Plus system, Amersham Pharmacia) using the manufacturer's protocol.

Reporter based quantification of viral replication: the present invention provides a reporter system to quantify adenoviral replication in real time by linking Green Fluorescent Protein (GFP) expression to the viral major late gene Fiber through an Internal Ribosome Entry Site (IRES). In brief, this replication deficient reporter virus, FFIG expresses GFP in a replication dependent manner when co-infected with a replicating adenovirus. For reporter experiments, cells are plated into 96-well plates at $1 \times 10^4$/well overnight, and co-infected the next day with various replication competent adenoviruses at different MOI of 5-10 pfu/cell and the reporter virus FFIG at an MOI of 10-20 pfu/cell. The GFP fluorescence signals are measured at the indicated time points using a multi-plate fluorometer (FLUOstar Optima Microplate Reader), utilizing an excitation wavelength of 485 nm+/−20 nm and an emission wavelength of 530 nm+/−25 nm. Background fluorescence is measured in cells which are infected with FFIG virus alone. GFP data are plotted as fold GFP induction relative to the mock infected cells. All samples are performed in either triplicate or quadruplicate with error bars representing the standard error of the mean.

3-(4,5)-Dimethylthiazol-2-yl)-5-(3-carboxy-methoxyphenyl)-2-(4-sulfophenyl)-2H-tetrazolium (MTS) assay: The metabolic viability of the cells was monitored using a MTS assay kit (CellTiter 96) from Promega (Madison, Wis.). Briefly cells are seeded onto 96-well plates and cultured in the presence of test agents for indicated time intervals. A mixture of MTS and phenazine methosulfate (an electron-coupling reagent; final concentrations 333 µg/ml and 25 µM, respectively) is added, and cells are incubated for 30 minutes at 37° C. Formazan formed from the reduction of MTS is quantified by measurement of absorbance of the medium at 490 nm using a microplate reader (All data have been normalized to the background signals).

EXAMPLE 2

Generation of Recombinant Adenoviruses

Northern Blot Analysis: Total RNAs are isolated from cells infected with adenovirus Ad5-RV004.21 carrying shRNAp21 at different time points using Trizol. Fifteen micrograms of total RNAs are resolved on 15% acrylamide/8M urea gel, transferred onto nylon membranes and UV cross-linked. Membranes are hybridized in the hybridization solution at 42° C. with [Gama $P^{32}$] labeled oligo designed against the processed sense strand of p21. The blots are autoradiographed with an intensifying screen at −80° C. for one day and scanned with Molecular Imager FX (Bio Rad).

Figure 9:
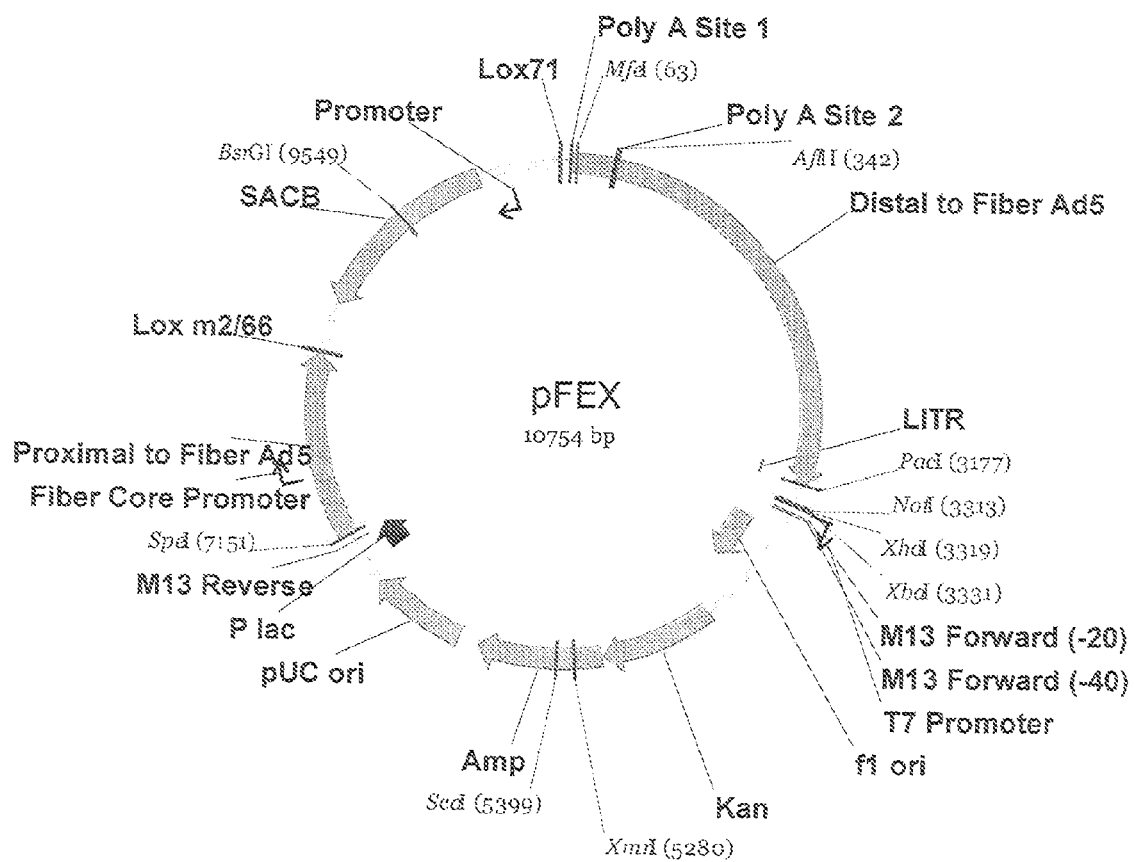
FIG. 9 shows an exemplary map of the pFEX system provided by the subject invention for combination with the shuttle vector RpS-TOAD-PSE/PBN-E1A.
Figure 10:
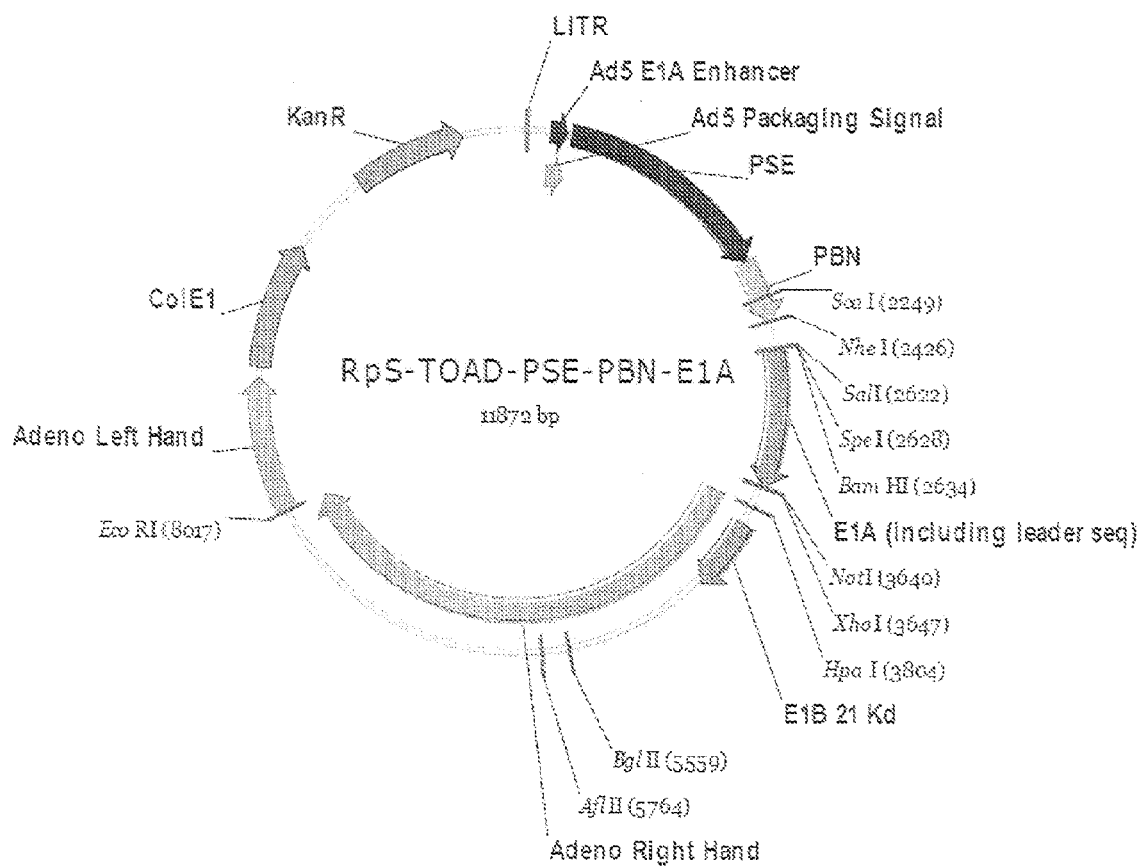
FIG. 10 shows an exemplary map of the shuttle vector RpS-TOAD-PSE/PBN-E1A provided by the subject invention.
Figure 11:
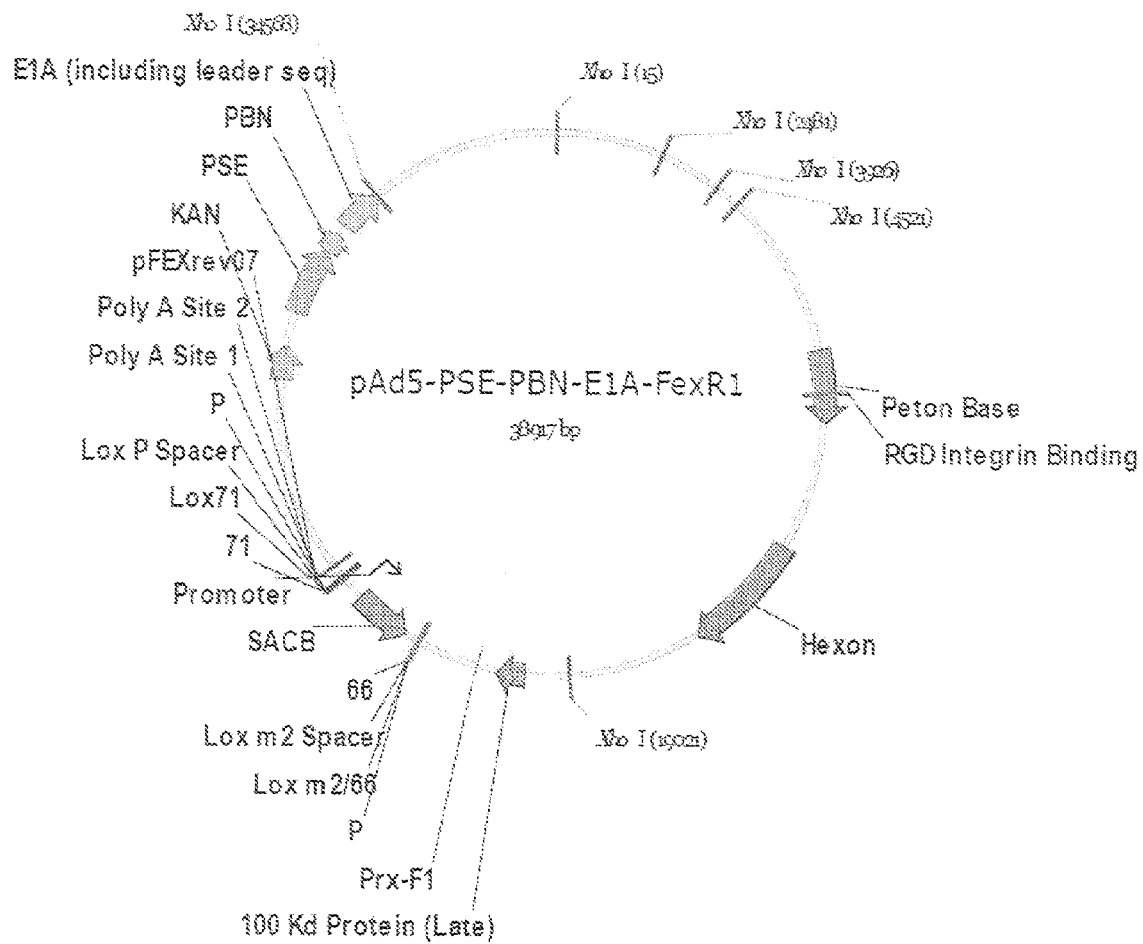
FIG. 11 shows an exemplary map of the pAd5-PSE/PBN-E1A-FEX-R1 vector provided by the subject invention. The pAd5-PSE/PBN-E1A-FEX-R1 vector can be generated by homologous recombination of pFEX with the shuttle vector RpS-TOAD-PSE/PBN-E1A in bacteria BJ5183.
Figure 13:
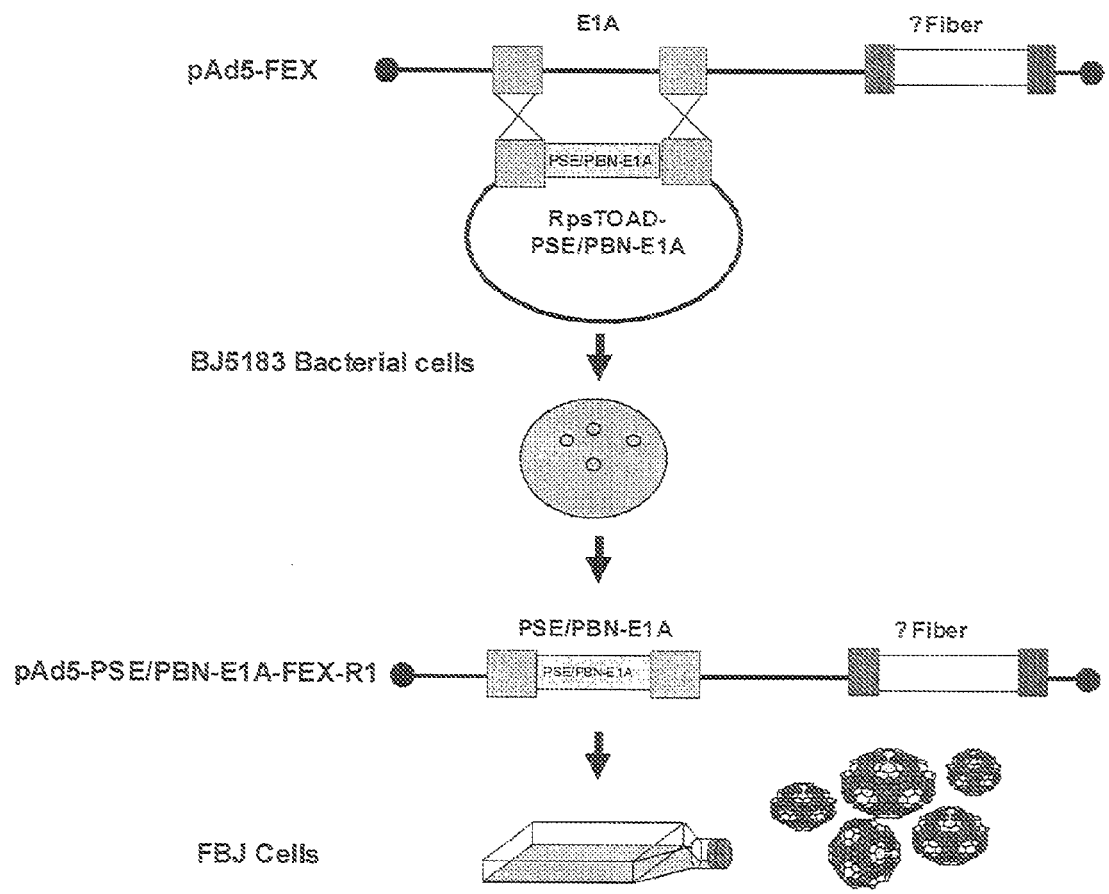
FIG. 13 shows an illustration of the recombination event employed by the subject invention to generate the pAd5-PSE/PBN-E1A-FEX-R1 vector.

Generation of Recombinant Adenoviruses: Ad5 wtAE3 (CN702) is an adenovirus type 5 with a deletion in E3 region. The present invention provides a prostate specific CRAd, Ad5-PSE/PBN-E1A (Ad5-RV004). Briefly shuttle plasmid RpsToad-PSE/PBN-E1A (illustrated in FIG. 10) that carries prostate specific enhancer and rat probasin promoter driving E1A is linearized with EcoRI restriction endonucleases. After gel purification the linearized RpsToad-PSE/PBN-E1A vector is transformed into the electro-competent AdEasier-1 (BJ5183-AD-1) cells for homologous recombination. The desired clones (pAd5-PSE/PBN-E1A) after screening are transformed into non-recombinant strain DH10B cells for large-scale DNA amplification. For viral propagation the recombinant plasmid pAd5-PSE/PBN-E1A is linearized with PacI and transfected into adenovirus packaging cell line DPL-S11 to generate recombinant adenoviruses. Virus amplification is done in the same DPL-S11 cell line. Similarly for generating a prostate specific conditionally replicating adenovirus (Ad5-RV004.21) that carries an anti-p21/Waf-1 shRNA after the Fiber region, an adenoviral pFEX system (illustrated in FIG. 9) is used to recombine a shuttle plasmid RpsToad-PSE/PBN-E1A (illustrated in FIG. 10) using homologous recombination between the two LTRs of the adenovirus in BJ5183 bacterial competent cells (the recombination event is illustrated in FIG. 13). After getting the desired recombinant, the Fiber-less viral DNA that carried prostate specific enhancer and rat probasin promoter (pAd5-FexPSE/PBN-E1A) is linearized with PacI and transfected into the Fiber expressing FBJ cell line to generate prostate specific pseudo-typed Ad5-FexPSE/PBN-E1A virus (illustrated in FIG. 11).

Figure 8:
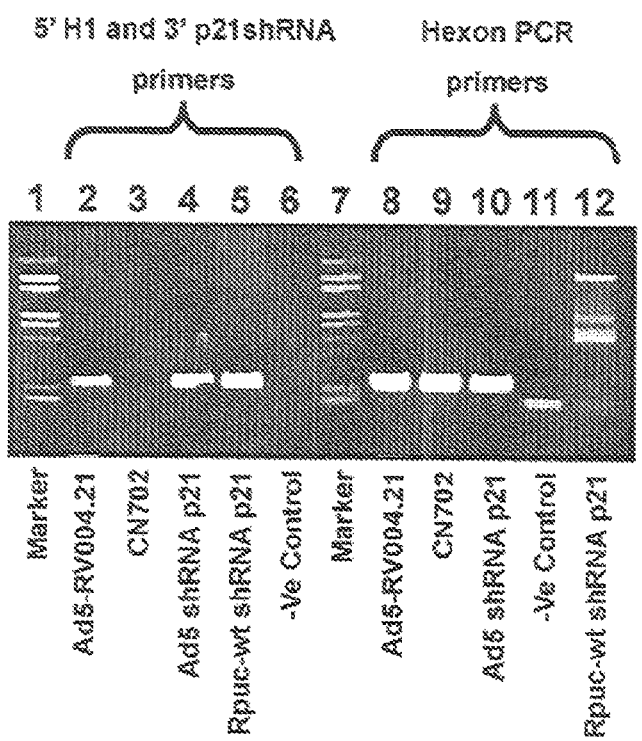
FIG. 8 shows detection of p21 shRNA sequence and replication competent adenovirus (RCA) in the Ad5-RV004.21 preps. PCR amplifications, using a set of primers specific to the H1 promoter and p21/Waf-1 region of shRNA, are used to confirm the presence of p21/Waf-1 shRNA sequences in Ad5-RV004.21 preps along with controls.
Figure 8:
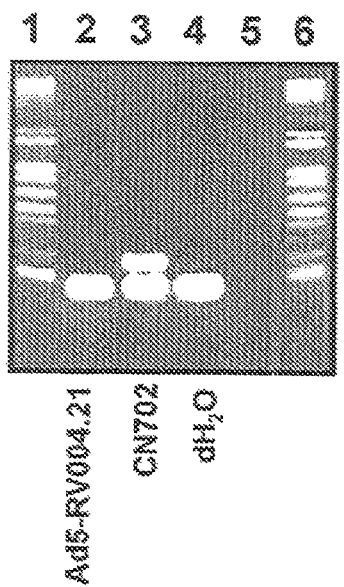
Figure 12:
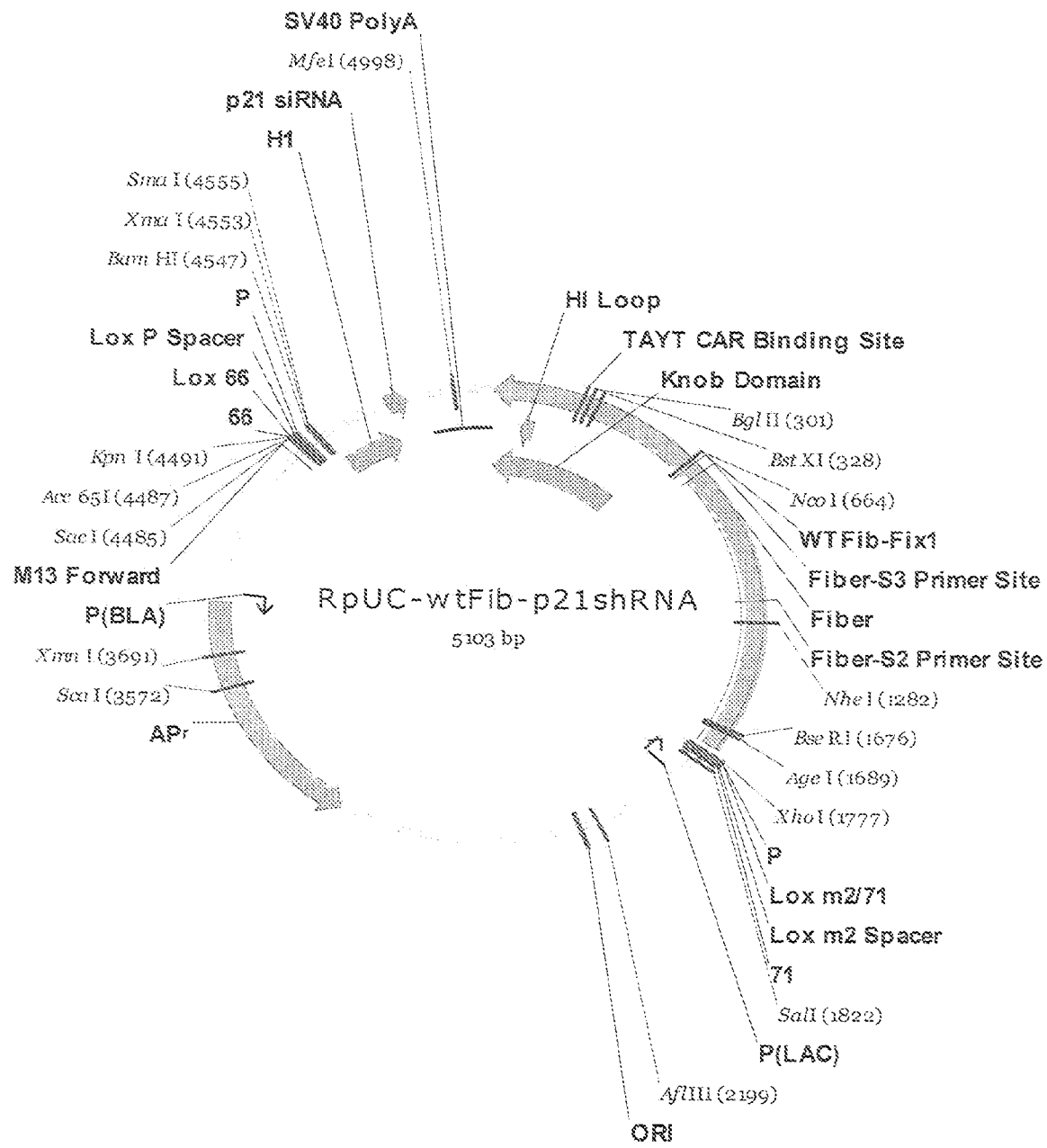
FIG. 12 shows an exemplary map of the RpUC-wtFib-p21shRNA vector provided by the subject invention. The shRNA against p21/Waf-1 is in Not 1 of the shuttle vector RpUC-wtFib.
Figure 14:
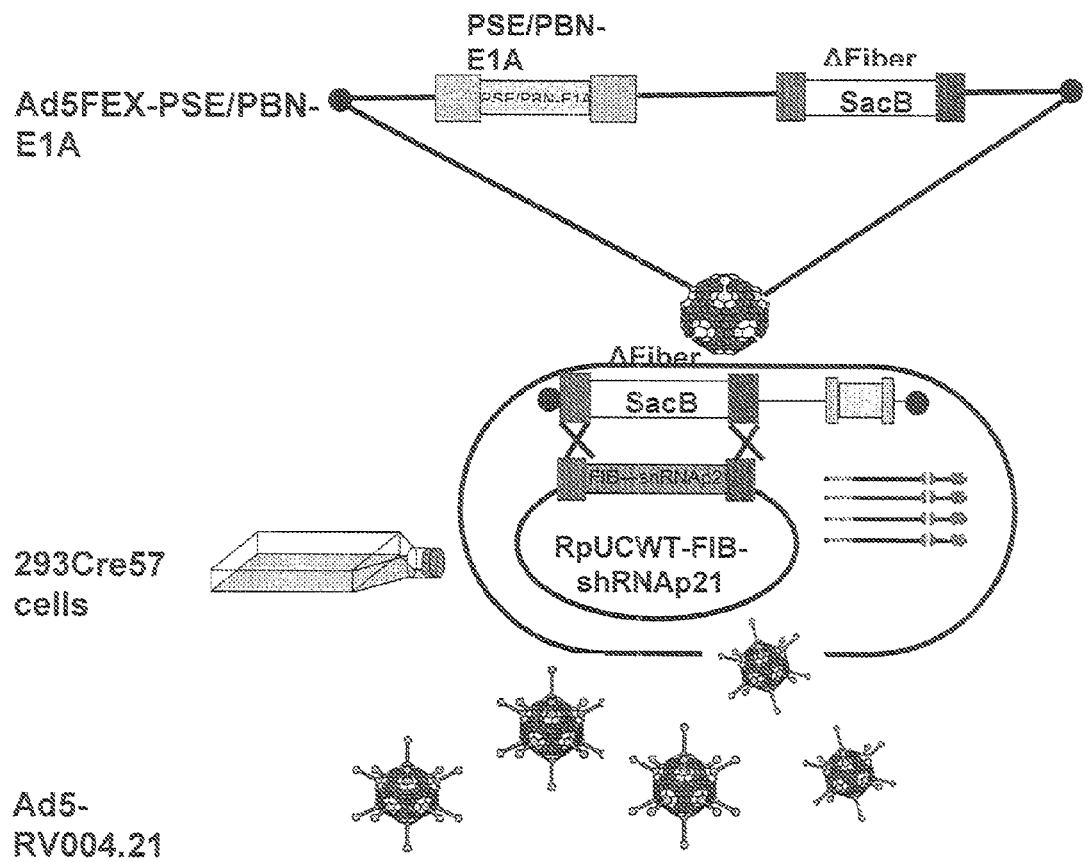
FIG. 14 shows an illustration of the recombination event employed by the subject invention to generate the Ad5-RV004.21 viruses.

The Ad5-RV004.21 that carries an anti-p21/Waf-1 shRNA and a wild type Fiber is produced by the transfection and infection experiment using a transient vector RpUC-WT-FIB shRNAp21 (illustrated in FIG. 12) and a pseudo typed Fiber-less adenovirus Ad5-FexPSE/PBN-E1A in 293Cre57 cells. Once Ad5-RV004.21 is made (generation of Ad5-RV004.21 viruses is illustrated in FIG. 14) and purified, RCA (replication competent adenovirus) is ruled out using PCR amplification with a set of primers E1A (5') (SEQ ID NO:3) 5'-CGT-TCCGGGTCAAAGTTGG-3' and E1A (3') (SEQ ID NO:4) 5'-CCTCCGTGGCAGATAATATGTC-3' spanning the wild type E1A promoter and E1A gene. PCR amplifications can be performed to confirm the presence of the anti-p21/Waf-1 shRNA in Ad5-RV004.21 preps using a set of primers P21 (5') (SEQ ID NO:5) 5'-GAACGCTGACGTCATCAA-3' and P21 (3') (SEQ ID NO:6) 5'-AAGTTCCATCGCTGGG-3' specific to the H1 promoter and a p21/Waf-1 region of the shRNA (see FIGS. 8A and 8B).

For the comparison of a single shRNA construct against Luciferace in two different regions of adenovirus, i.e., E1 region and Fiber region, two different replication deficient adenoviruses, Ad5-Track-U6-shRNALuc or Ad5-Fex-U6shRNALuc are made utilizing either AdEasy-1 or pFEX systems. Briefly shRNA against Luciferase in E1 region of the adenovirus is cloned in BglII/Not1 site of the shuttle pAdTrack plasmid. Shuttle plasmid carrying shRNA against the Luciferase (pAd-TrackshRNA-Luc) is than recombined with AdEasy-1 backbone in bacterial strain BJ5183 using homologous recombination. Viruses are made and amplified after transfection of the linearized recombinant vector pAd5-Track-U6-shRNALuc into the DPL cells. Unlike Ad5-Track-U6-shRNALuc virus that carries Luc shRNA in the E1 region, the Ad5-Fex-U6shRNA-Luc has shRNA against Luciferase after the Fiber region by taking advantage of the pFEX system. The shRNA against Luciferase is cloned into the Not1 site of a shuttle plasmid Rpuc-WTFib (illustrated in FIG. 12). Ad5-Fex-U6shRNALuc virus is made by tranfection and infection of a pseudotyped Ad5-FexTrack virus (0.5 MOI) together with shuttle plasmid Rpuc-WTFib shRNA-Luc (4 μg/ml) and pUC-Cre (2 μg/ml) in DPL-S11 cells.

Viral amplification: Viral output to input assays are performed using Adeno-X Rapid Titer Kit (Clontech Laboratories, Inc., Mountain View, Calif.). Briefly, cells are infected with adenovirus (1 MOI) in six well plates. Seventy two hours post infection, cells are harvested in the same medium and subjected to three rounds of freeze thaw cycles. Total infectious viruses are measured by tittering them on HEK293 cells according to the Adeno-X Rapid Titer Kit protocol. The "amplification ratio" of a virus produced from an infected cell (Output) to the amount originally used to infect the cells (Input) are then determined and reported as the output to input ratio.

Luciferase Assay: $1 \times 10^4$ cells/well are plated in a 96-well plate one day before infection. Cells are then infected with adenovirus carrying Luciferase (1 MOI) together with either adenovirus carrying shRNA against Luciferase in the E1A region or after the Fiber region (10 MOI). The Luciferase assays (Dual-Glo Luciferase Assay System, Promega, Wis.) are performed at 24-48 hours post infection. All of the shRNA knock-down experiments are performed in quadruplets and normalized to the total GFP measured in the cells. Luciferase activity is reported as % relative light forming units normalized to GFP.

EXAMPLE 3

BALB/C-Nude Mice and Tumor Implantations

Four to six-week-old athymic BALB/c nude male mice, weighing approximately 14 g can be obtained from Harlan (USA). Mice are quarantined for a minimum of 5 days in the SPF Grade Animal House under a 12 hours light/dark cycles at 24-25° C. with a relative humidity of 50-55%. Tumors are established by subcutaneous (s.c.) injection with C4-2 cells ($1 \times 10^6$) resuspended in 1× phosphate buffered saline (pH 7.4; BioSource, Rockville, Md.) mixed 1× with Matrigel (BD Biosciences, Palo Alto, Calif.), in both dorsal flanks of the animals. Once palpable tumors are established, animals are randomized into control and treatment arms.

Statistical Analysis: All experiments are done in triplicate or quadruplicate and plotted with standard errors of the mean. All statistical analysis is performed using Prism 4.0 (GraphPad, Inc.) or Excel running on IBM-PC compatible computer on the Windows XP operating system. Statistical comparisons for paired data are analyzed by the student's t-test for the in vitro assays while ANOVA are used to analyze the statistical significance for in vivo xenograft models. Statistical significance was defined as $p<0.05$.

EXAMPLE 4

RNA Interference Against p21/Waf-1 Enhances Adenovirus Replication

Figure 1B:
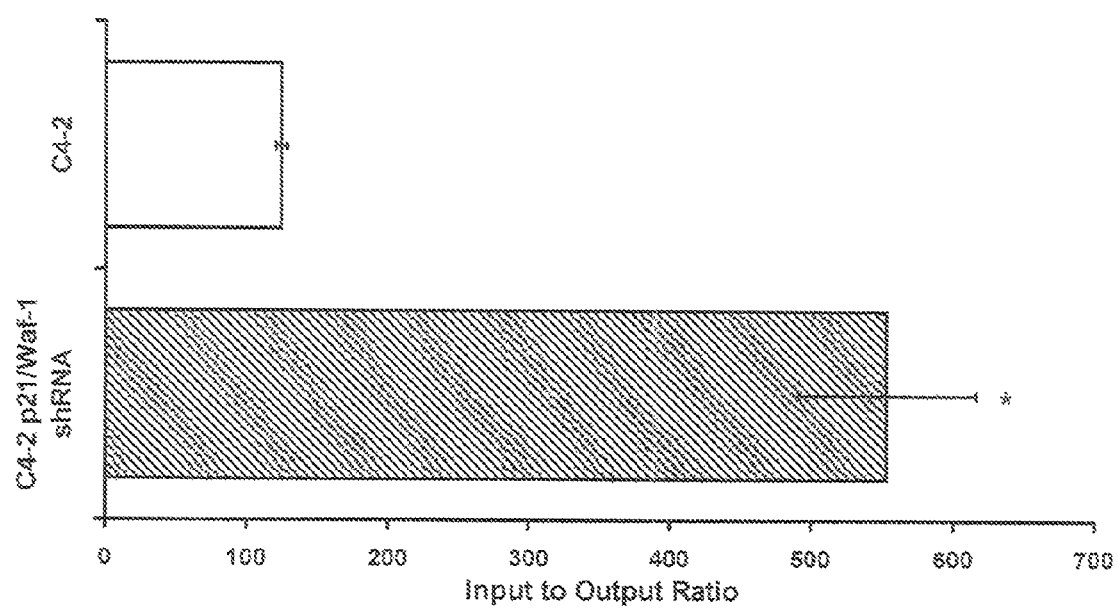
FIGS. 1B and 1C show that a prostate specific conditionally replicating adenovirus (Ad5-RV004) replicates better in p21/Waf-1 knockdown C4-2 (FIG. 1B) and LAPC-4 cells (FIG. 1C) compared to the control cell lines.
Figure 1C:
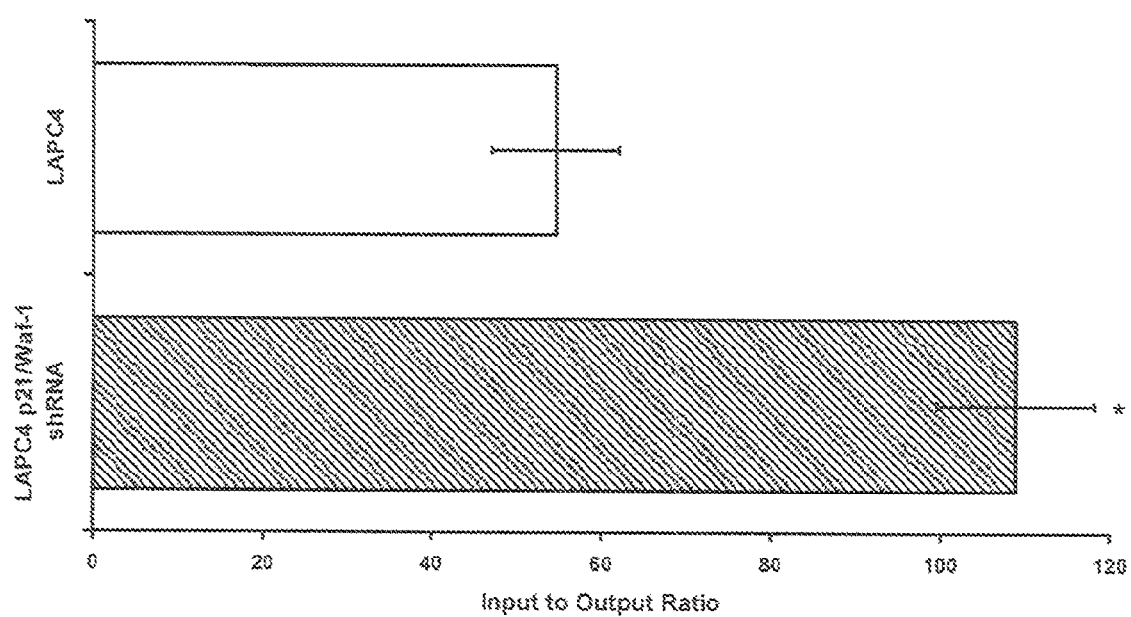
Figure 1D:
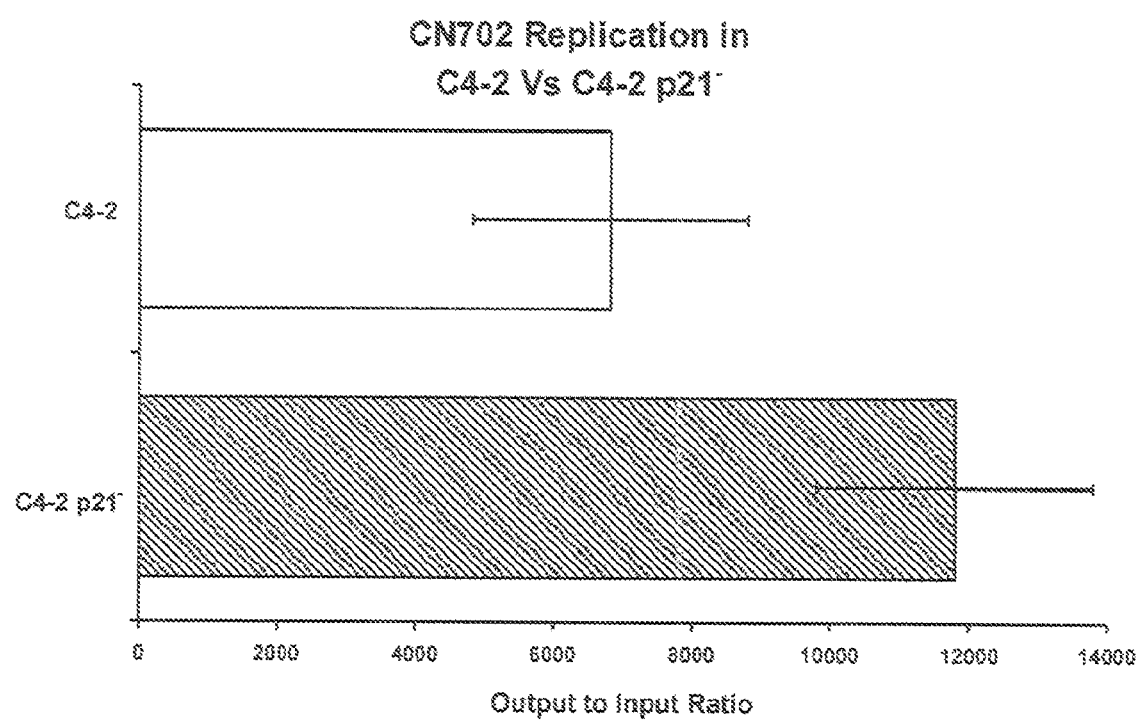
FIG. 1D shows an output to input assay with CN702 Virus in p21/Waf-1 knockdown and intact C4-2 Cells. Viral output of CN702 (MOI1) from p21/Waf-1 knockdown and control C4-2 cell lines are tittered and reported as output to input ratios at 72 hours PI. Data plots represent output to input ratio from three individual experiments at 72 hours PI and is given as the mean±S.E of triplicate samples.

The present invention provides that histone deacetylase inhibitors (HDACI) can enhance the expression of adenovirus receptors for cancer gene therapy. The present invention provides that more potent oncolytic viruses can be generated in cells which express short hairpin RNA (shRNA) expression cassettes which target p21/Waf1. The present invention provides anti-p21/Waf-1 shRNA and control vectors to establish two prostate cancer cell line models, C4-2 and LAPC-4, with native or reduced p21/Waf-1 expression (FIG. 1A). These cell lines are infected with equal multiplicity of infection (MOI) of a prostate-specific CRAd, Ad5-RV004, and total viral output is quantified. Cells with reduced p21/Waf-1 expression produce two- to five-times more infectious adenovirus as compared to vector containing cells (FIGS. 1B and C). Similarly, wild type adenovirus (CN702) virus yields are nearly doubled in cell lines with reduced p21/Waf-1 expression (FIG. 1D). These results suggest that oncolytic adenoviruses armed with anti-p21/Waf-1 shRNA expression cassettes can enhance replication kinetics and therapeutic efficacy.

Figure 2A:
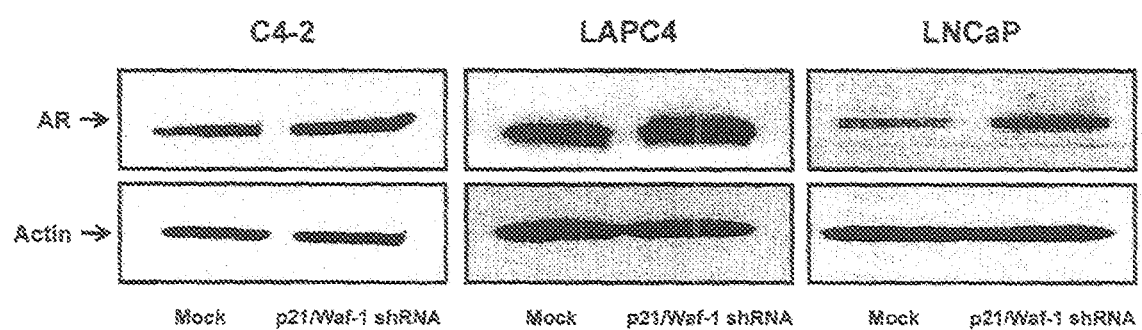
FIG. 2A shows a Western blot analysis for over expression of AR in stable p21/Waf-1 knockdown C4-2, LAPC-4 and LNCaP cells, beta actin was included to serve equal amount of loading across the wells. Firefly luciferase assay is performed to study the induction of AREs based prostate specific enhancer and rat probasin promoter (PSE/PBN) in p21/Waf-1 knockdown C4-2 or control cells. Over expression of the same shRNA construct against p21/Waf-1 in stably selected p21/Waf-1 knockdown C4-2 cells can show further increase in the promoter inducibility suggesting the dose dependent response of the p21/Waf-1 knockdown in AR induction. Firefly luciferase activity is normalized to Renilla luciferase expression and plotted as Fold luciferase expression and illustrated in FIG. 2B. Data set represent mean±S.E of the quadruplicate experiment.
Figure 2B:
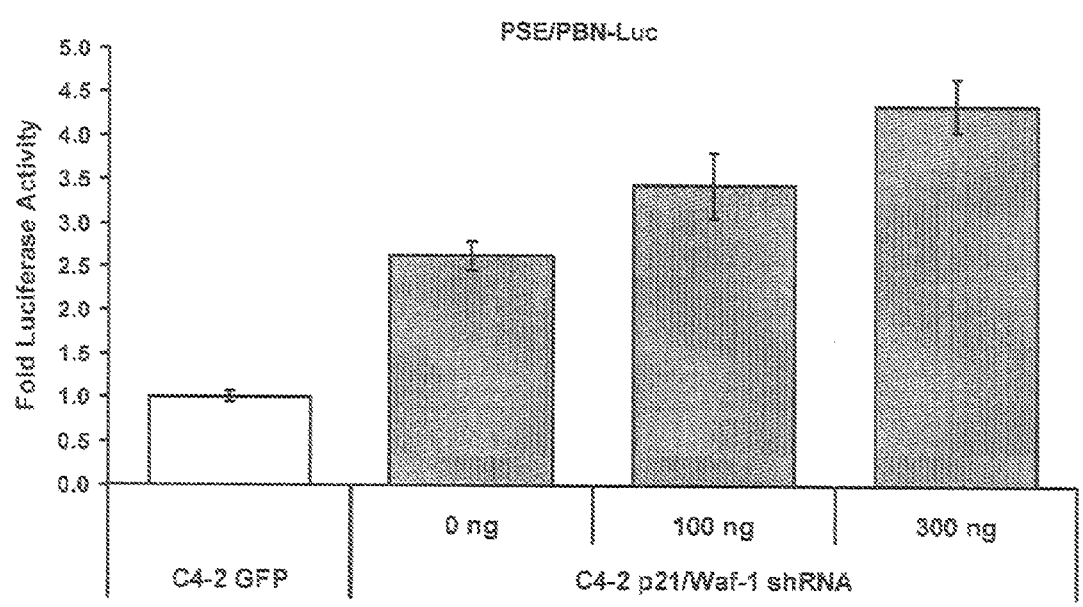
FIG. 2 shows induced expression of Androgen Receptor (AR) in p21/Waf-1 knockdown cell lines.

The present invention provides that knocking down p21/Waf-1 can induce prostate specific promoter (PSP) by up-regulating Androgen Receptor (AR) expression. Typically replacing viral promoters with tissue specific promoters in their backbones can make them weaker in terms of replication and potency. The present invention provides that knocking down p21/Waf-1 with shRNA is linked to the up-regulated expression of the Androgen Receptor. As shown in FIG. 2A, C4-2, LAPC4 and LNCaP cells with stable knockdown for p21/Waf-1 expression had higher AR expression compared to the mock cells. To further verify that this increase in the total AR expression is indeed a functional increase; a reporter assay is performed using rat probasin promoter and prostate specific enhance (PSE/PBN) driving luciferase expression. Briefly stable p21/Waf-1 knockdown C4-2 cells or control cells are transfected with equal amounts of plasmids (pRL-PSE/PBN-FLuc together with a renella luciferase expressing plasmid pCMV-RL for normalization). C4-2 cells with p21/Waf-1 knockdown had 2 fold induced expression of Luciferase compared to the mock C4-2 cells (FIG. 2B). The present invention provides that this induced expression of the PSE/PBN promoter in p21/Waf-1 knockdown cells is dose dependent as further over expression of the same p21/Waf-1 shRNA construct (pSuper-puro-EGFP-shRNA p21/Waf-1) in these stable C4-2 p21/Waf-1 knockdown cells can show an increase in the total amount of Luciferase expression. This data demonstrates that shRNA against p21/Waf-1 can be responsible for the induced expression of the ARE based PSE/PBN promoter and can be translated in the construction of gene therapy vector provided by the present invention.

Figure 7:
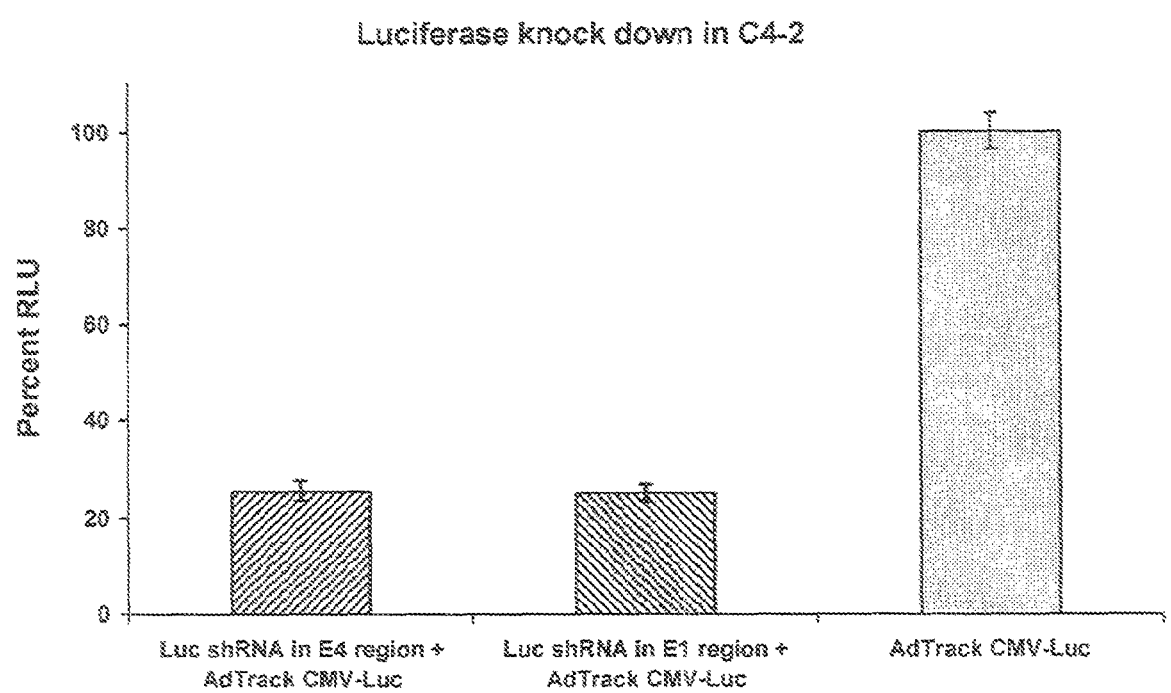
FIG. 7 shows a comparison between the shRNA constructs against Luciferase in two different regions of Adenovirus for functional knockdown. Small hairpin RNA (shRNA) against Luciferase in the E1A region and Fiber region of adenovirus driven by U6 promoter is compared for functional knockdown assay of the luciferase expression in C4-2 cells. C4-2 cells are co-infected with Ad5-TrackCMV-Luc (1 MOI) together with an adenovirus that carries shRNA construct against luciferase after the Fiber region (AdTrack-Fex-shRNA-Luc) or in E1 region (Ad-Track-shRNALuc) of the virus at 10 MOI for 48 h. The luciferase expression is plotted as percent RLU after normalizing to the adenoviral GFP expression. There is no significant difference in the knockdown between the two virus using student t-test ($p<0.05$).
Figure 15:
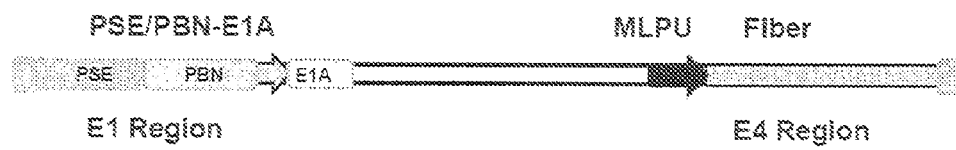
FIG. 15 shows an illustration of the difference between Ad5-RV004 and Ad5-RV004.21.
Figure 15:
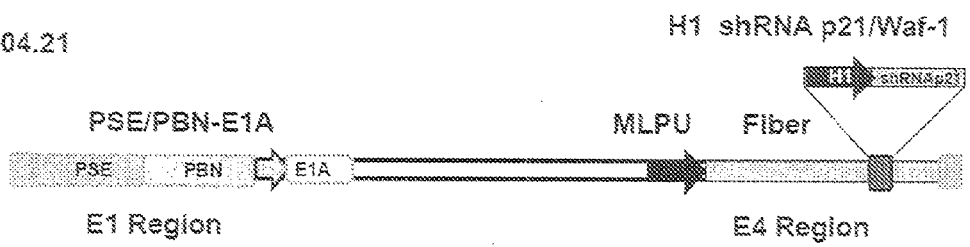

The present invention provides construction and replication kinetics of the prostate specific CRAd virus carrying shRNA against p21/Waf-1. The present invention provides that p21/Waf-1 protein interacts directly with adenoviral E1A protein, resulting in an inactivation of p21 CDK activity. The present invention also provides that replicating adenovirus which expresses an anti-p21/Waf-1 shRNA can enhance replication in prostate cancer cells. Alternative regions for expression of the shRNA cassette can be tested. For example, most CRAds utilize a tissue or cancer selective promoter upstream of the viral immediate early or early gene that is E1A or E1B in the E1 region for tissue specificity. Alternatively, the natural viral early gene promoters are retained and cancer specificity is achieved by modifications to the viral E1A or E1B genes. The present invention provides a head to head comparison of the same shRNA construct against Luciferase in both the E1 versus the Fiber region of adenovirus. HEK293 cells infected with over expressing Luciferase adenovirus (1MOI) are co-transduced with a non replicative viruses that carry shRNA against Luciferase either in E1 (AdTrack shRNA-Luc) or Fiber region (AdTrack-Fex-shRNA-Luc) at MOI of 10. After 48 hours, plates are read for Luciferase and normalized to the viral GFP expression. As shown in FIG. 7, both viruses are able to knockdown luciferase expression. The present invention provides that the Fiber gene region is a viable region for housing shRNA expression cassettes in CRAds. A prostate specific CRAd Ad5-RV004.21 is generated. This CRAd Ad5-RV004.21 expresses E1A gene under the control of Human prostate specific enhancer and rat probasin promoter (PSE/PBN) while the shRNA against p21/Waf-1 driven by HI promoter is placed after the Fiber region (see FIG. 15).

Figure 3A:
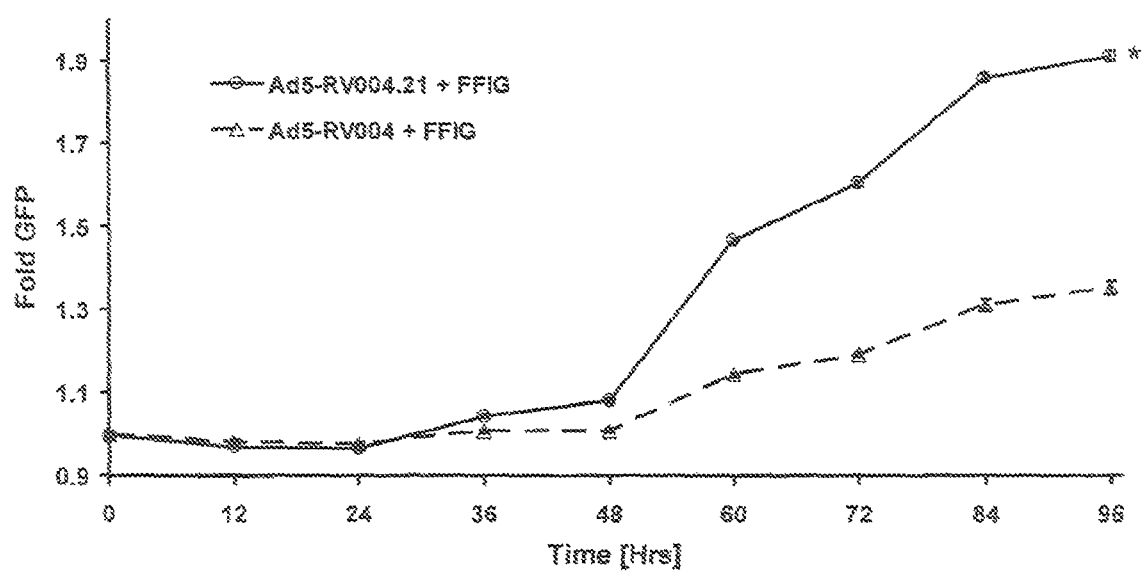
FIGS. 3A and 3B show that, in both LNCaP and C4-2 cells, Ad5-RV004.21 can provide higher fold replication as compared to the Ad5-RV004. LNCaP or C4-2 cells treated with VPA at different concentration (0, 0.6, 1.2 mM) are infected with ether Ad5-RV004.21 or Ad5-RV004 (5 MOI) in the presence of a reporter FFIG virus (10 MOI). GFP expression is measured and plotted as fold induction of GFP over the FFIG background.
Figure 3B:
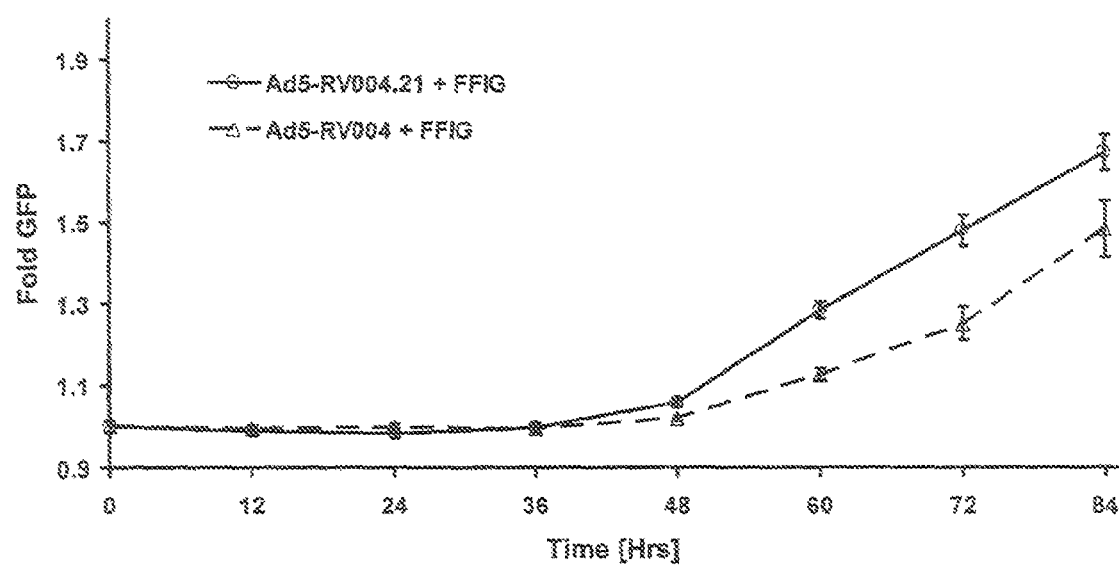

To demonstrate that Ad5-RV004.21 (which contains an shRNA against p21/Waf-1) is able to replicate better than Ad5-RV004 (lacking the anti-p21/Waf-1 shRNA), the FFIG reporter system can used according to the present invention. This FFIG reporter system places a GFP gene under the control of the major late promoter (MLP), enabling the ability to measure viral replication in real time in a non-invasive high-throughput assay. LNCaP cells plated at a density of $5 \times 10^4$ cells per well are infected with MOI of 5 with test viruses (Ad5-RV004.21 or Ad5-RV004) in the presence of a reporter virus FFIG (MOI 10) in complete medium supplemented with 5 nM of R1 881. As shown in FIG. 3, there is a significant difference in the replication kinetics between the two viruses ($p<0.05$) which started as early as 48 hours post infection (FIG. 3A). This demonstrates that the CRAd virus that carries an shRNA against p21/Waf-1 (Ad5-RV004.21) replicates faster than a virus without the anti-p21/Waf-1 shRNA (Ad5-RV004) in LNCaP cells. Similar results of enhanced Ad5-RV004.21 viral replication over Ad5-RV004 are also obtained in the androgen independent C4-2 cell line (FIG. 3B).

Figure 3C:
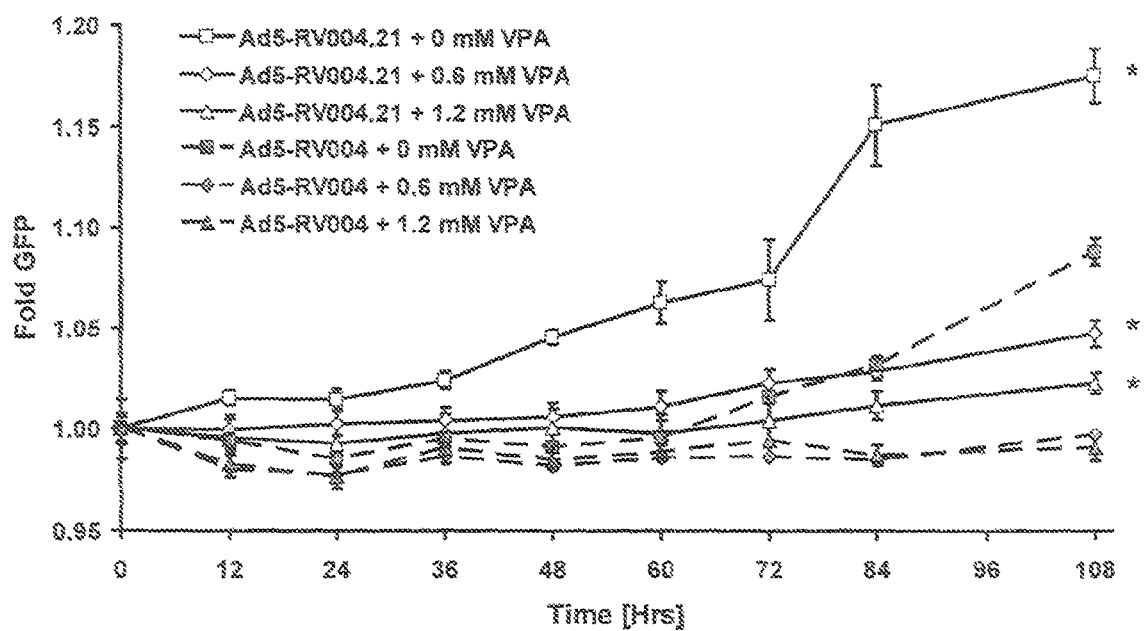
FIGS. 3C and 3D show that, in both cells lines, Ad5-RV004.21 which carries shRNA against p21/Waf-1 is able to replicate faster than Ad5-RV004 which lacked p21/Waf-1 shRNA.
Figure 3D:
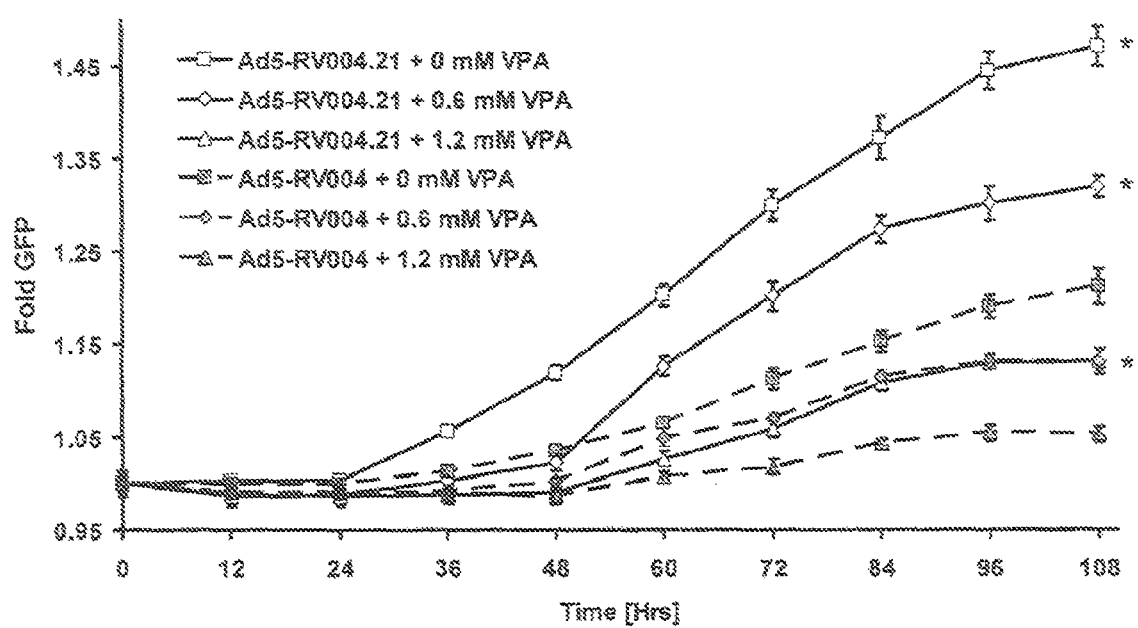

Since HDACI suppresses viral oncolysis in a process which involves but is not totally dependent on HDACI induction of p21/Waf-1, the present invention provides that shRNA based p21/Waf-1 knockdown can overcome HDACI suppression of viral replication. LNCaP and C4-2 cells are infected with either Ad5-RV004.21 or Ad5-RV004 in the presence of different concentrations of VPA (0, 0.6, or 1.2 mM). As shown in FIGS. 3C and 3D, Ad5-RV004.21 can replicate better than Ad5-RV004.

EXAMPLE 5

Dose-Dependent Down-Regulation of p21/Waf-1 by Ad5-RV004.21

Figure 4A:
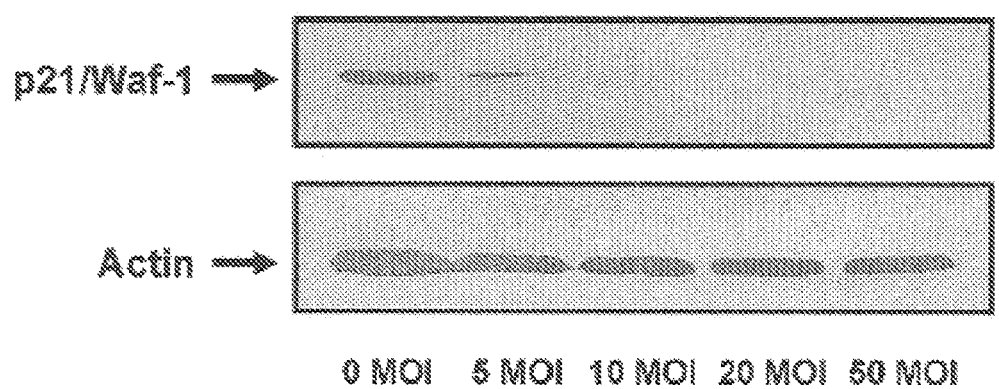
FIG. 4A shows a Western blot for knock down of p21/Waf-1 expression in C4-2 cells with increasing MOIs (0, 5, 10, 20, and 50) of Ad5-RV004.21 virus after 24 hours of infection.
Figure 4B:
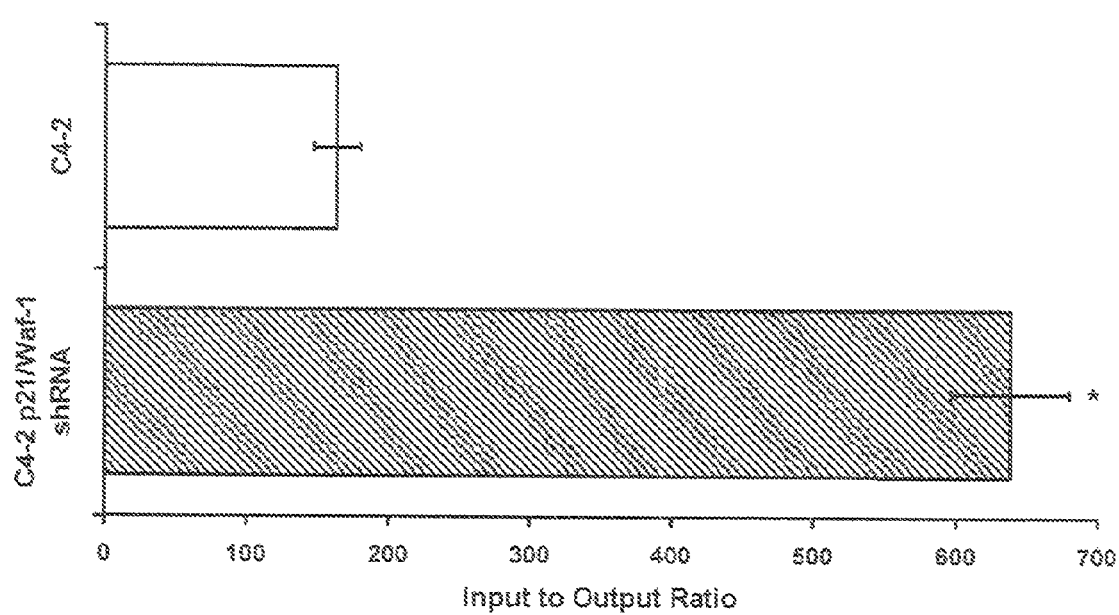
FIG. 4B shows an output to input assay of the Ad5-RV004.21 virus from cells stably expressing shRNA against p21/Waf-1 72 hours PI. Northern blot analysis is performed on the total RNA extracted from the stably expressing p21/Waf-1-shRNA C4-2 cells infected with Ad5-RV004.21 (MOI 0.5).
Figure 4C:
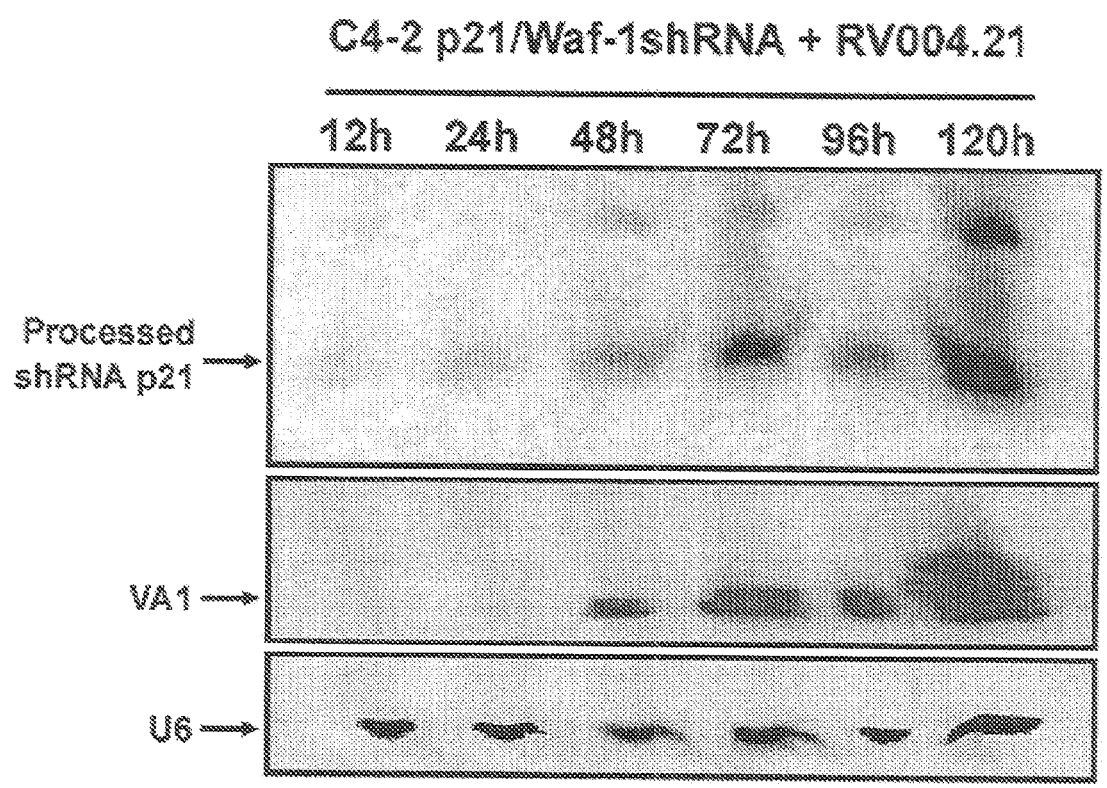
FIG. 4C shows that a none-coding VA1 adenoviral RNA is probed with VA1 probe that accounts for the presence of replicating virus and a probe complementary to U6 is used to ensure equal amount of loading across different lanes.

Since gene silencing using RNA interference can generally work in a dose dependent manner, the present invention provides that an adenovirus carrying shRNA against p21/Waf-1 can also function in a dose dependent manner. C4-2 cells are infected with Ad5-RV004.21 at different MOIs. Cells are harvest in RIP A buffer approximately 24 hours post-infection for Western blot analysis. As shown in FIG. 4A, levels of p21/Waf-1 protein can be completely decreased to undetectable levels with high MOIs of the Ad5-RV004.21 in C4-2 cells. The present invention further provides the use of C4-2-p21/Waf-1 shRNA knockdown or control cell lines and infected them with Ad5-RV004.21. Virus titer assays are performed 96 hours post infection on HEK293 cells. As shown in FIG. 4B, viral titers recovered from the stable p21/Waf-1 knockdown cells are significantly higher than that of control C4-2 cells. To explain these higher titers of Ad5-RV004.21 in cells which are selected to express an anti-p21/Waf-1 shRNA, the levels of the processed anti-p21/Waf-1 shRNA in the adenoviral infected cells are evaluated. Total RNA from the C4-2-p21/Waf-1 cells infected with Ad5-RV004.21 at 0.5 MOI are subjected to Northern blot analysis and probed with an oligo designed against the processed sense strand of the anti-p21/Waf-1 shRNA. The same blot is used for an endogenous adenoviral Pol III gene (VA1) which results in a non-coding RNA as a viral control as well as endogenous U6 RNA, as a cellular control. As shown in the FIG. 4C, there is a tremendous increase in the amount of the processed p21 shRNA over time compared to the initial 12-hours infection. Similarly, higher levels of VA1 are also detected over time in these C4-2-p21/Waf-1-shRNA cells. The high levels of processed anti-p21/Waf-1 shRNA in the cell lines that already expressed shRNA against p21/Waf-1 might explain higher titers in our output to input viral titer assays. In other words, the stable p21/Waf-1 shRNA C4-2 cells are not completely devoid of basal p21/Waf-1 expression and even minor basal expression of p21/Waf-1 can have profound effects on viral replication.

Figure 5A:
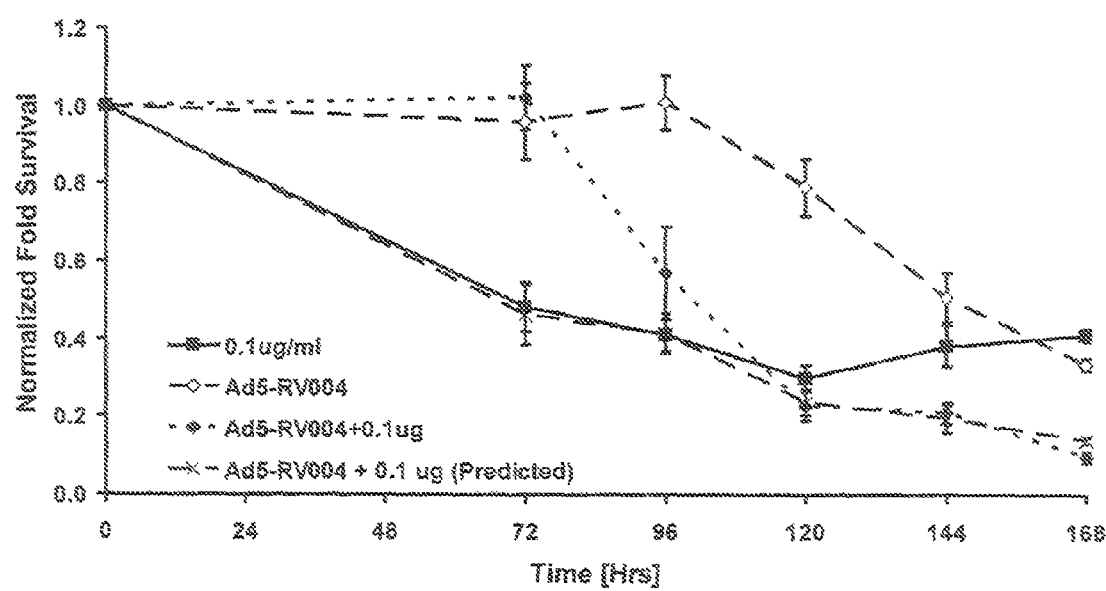
FIGS. 5A and 5B show growth inhibition and cytotoxicity of C4-2 cells treated with Ad5-RV004 (MOI=2) (FIG. 5A) or Ad5-004.21 (MOI=2) viruses (FIG. 5B) alone, or in combination with Adriamycin (0.1 µg/ml) was accessed by MTS assay at different time points (24 hours to 168 hours) and plotted as fold survival over background. Dotted line represents the predicted combined killing of the virus and drug. Data shown represent mean±S.E of the quadruplicate experiment.
Figure 5B:
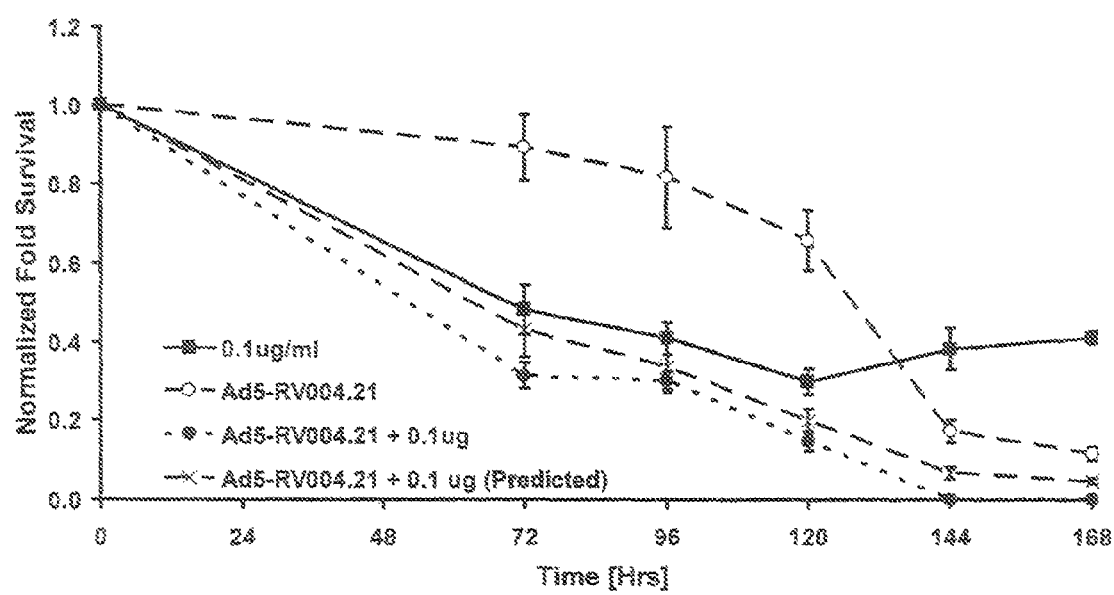

Combinatory studies of Adriamycin with Ad5-RV004.21 or Ad5-RV004 virus in C4-2 cells: Combination treatment of viruses with radiation or chemotherapy hold promise as a new strategy for cancer treatment. However, there are reports of attenuated cytotoxicity of CRAds when combined with chemotherapies (e.g., doxorubicin). To investigate the oncolytic activity of Ad5-RV004 or Ad5-RV004.21 in the presence of Adriamycin, C4-2 cells are infected with either Ad5-RV004 or Ad5-RV004.21 (MOI=2) in the presence or absence of adriamycin (0.1 μg/ml) in 96 well plates. Cell cytotoxicity is measured by MTS assay after 72 hours of treatment and followed every 24 hours for a total of 7 days. All treatments are normalized to background MTS treated media and plotted as a fold decrease in cell survival to the untreated control C4-2 cells. Data for the Ad5-RV004 or Ad5-RV004.21 can be plotted separately in the presence or absence of 0.1 μg/ml adriamycin. The predicted value for the combinatory effect can be calculated and is given by the dotted gray line. As shown in FIG. 5A, treatment of the adriamycin alone can kill almost 50% of the C4-2 cells by 72 hours of treatment. In Ad5-RV004 infected cells, the oncolysis of the infected cells is not seen till 120 hours PI and when both treatments are combined, their additive effect became obvious by 168 hours in C4-2 cells (FIG. 5A). On the other hand, C4-2 cells infected with Ad5-RV004.21 alone can kill about 20% of the infected C4-2 cell by 96 hours (FIG. 5B), and when both treatments are combined together, a super-additive (synergistic) effect is observed from the beginning of the treatment as shown by the closed circles (FIG. 5B). This super-additive (synergistic) effect of the Ad5-RV004.21 in the combinatory studies appears to be the direct result of the p21/Waf-1 shRNA which enhances drug-induce cell death.

EXAMPLE 6

In Vivo Oncolytic Activity of the Prostate Specific Ad5-RV004.21 Virus

This example demonstrates the benefit of adenoviral p21/Waf-1 knock-down of the present invention by comparing the oncolytic activity of Ad5-RV004.21 versus the non-shRNA containing Ad5-RV004 and the E3 deleted wild type adenovirus CN702 along with controls (buffer only and the replication defective Luciferase expressing adenovirus Ad5-RV002-F-Luc virus). C4-2 cells are subcutaneously inoculated into the dorsal rear flank region of athymic nude mice as described above. When tumor volume reaches approximately 0.2 cm$^3$, animals are randomized into four groups. Equal number of infectious viruses (i.e., 1×10$^8$ plaque forming units/tumor of either CN702, Ad5-RV004.21, Ad5-RV004, Ad5-RV002-F-Luc virus, or mock infection-phosphate-buffered saline) are administered intra-tumorally on day 1, 4 and 7.

Figure 6A:
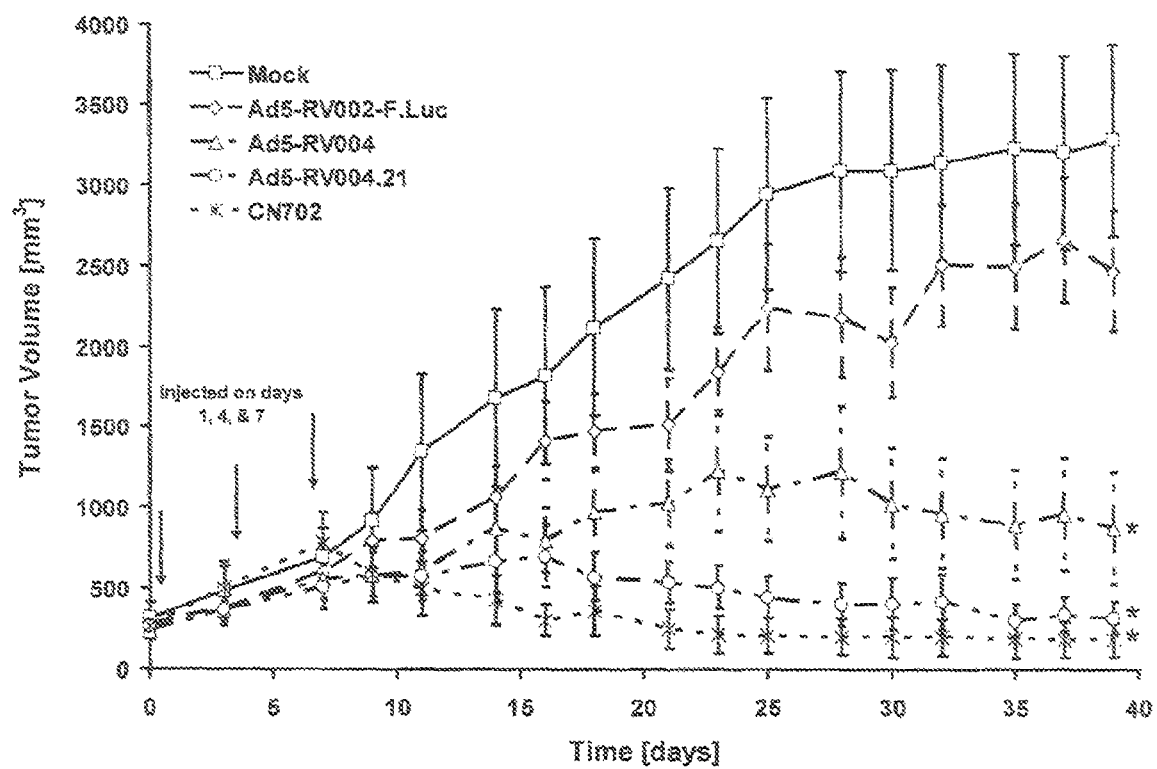
FIG. 6A shows that there is a significant difference between the tumor volumes in animals that were treated with wild type CN702 virus and Ad-RV004 virus ($P<0.05$) however no significant difference was observed in CN702 versus Ad5-RV004.21 treated animals ($P>0.05$). Kaplan-Meier plot showing survival of mice bearing s.c C4-2 tumor xenografts treated intra-tumorally with different viruses (CN702, Ad5-RV004, Ad5-RV004.21 or Ad5-002-F-Luc) or PBS. Animals are sacrificed when tumor area is $>2.0$ cm$^2$. A median survival versus time is evaluated using a log-rank test ($P<0.05$). All mock treated groups (Ad5-RV002-F-Luc or PBS) do not survive beyond 60 days of treatment, animals treated with CN702 (wild type virus) have 100% survival of while 40% of the Ad5-RV004 (n=5) and 85% of Ad5-RV004.21 treated animals survive beyond 100 days of treatment.
Figure 6B:
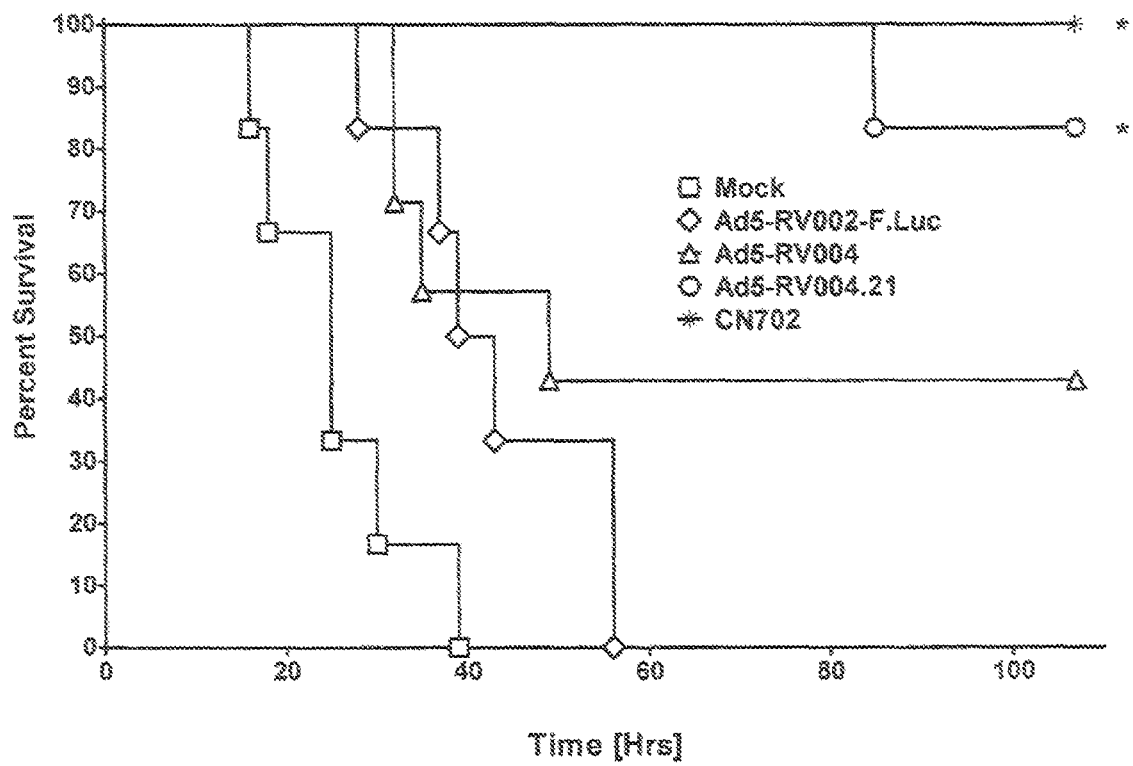
FIG. 6B shows that there is a significant difference in the survival of the PBS treated mocks versus the three Ad5-RV004, Ad5-RV004.21 and CN702 viral treatment groups, or Ad5-RV002-F.Luc Control virus versus CN702 or Ad5-RV004.21 treated animals. However no statistical difference is observed between the Ad5-RV002-F.Luc controls treated group versus Ad5-RV004 treated animals.

Tumor volume is measured every third day for 35 days and plotted as shown in FIG. 6A. Profound tumor growth is observed in the PBS control and in replication incompetent Ad5-RV002-F-Luc virus, with tumor volume approaching the maximum allowable size of 2.0 cm$^3$ by end of 24th day. Although, Ad5-RV004 suppresses the tumor growth in a statistically significant manner as compared to the control groups, this activity is not as dramatic as the Ad5-RV004.21 treated animals. Ad5-RV004.21 virus is able to suppress xenograft tumor growth similarly to that of wild type (CN702) virus and there is no significant difference between the CN702 and Ad5-RV004.21 treated tumors. The survival benefit of these animals treated with either Ad5-RV004 or Ad5-RV004.21 viruses is also compared. Animals are monitored daily for 100 days for signs and symptoms of any weakness or ulcerative tumors and are removed either after they die naturally or exhibit a heavy tumor burden (when tumor sizes were >2.0 cm$^3$). Survival is evaluated by Kaplan-Meier analysis and groups compared by the log-rank test using a p<0.05 as a cutoff for statistical significance. As shown in FIG. 5B, all negative control groups (Ad5-RV002-F-Luc or PBS) die within 60 days of treatment. However, 40% of the Ad5-RV004 (n=5) treated mice survive within duration of the experiment (>100 days) compared to 85% and 100% survival of Ad5-RV004.21 and CN702 treated animals.

A significant difference is found between the PBS treated mocks versus all three Ad5-RV004, Ad5-RV004.21 and wild type CN702 treatments. However, when all the viral treated groups are compared to the non-replicative Ad5-RV002-F.Luc treated animals, only Ad5-RV004.21 and wild type CN702 treated groups are found significant and no statistical significance are observed between the Ad5-RV002-F.Luc controls versus Ad5-RV004 treated animals (FIG. 5B). This phenomena of enhanced tumor suppression associated with improved survival by Ad5-RV004.21 compared to Ad5-RV004 appears to be a direct result of p21/Waf-1 knockdown.

Although the invention has been described with reference to the above example, it will be understood that modifications and variations are encompassed within the spirit and scope of the invention. Accordingly, the invention is limited only by the following claims.

What is claimed is:

1. A method for enhancing oncolytic adenovirus replication in prostate cells comprising: contacting the prostate cells with an adenovirus construct comprising a nucleic acid sequence encoding an shRNA in the E1 region or the Fiber region; and a nucleic acid sequence encoding a prostate specific promoter or a prostate specific enhancer, wherein the shRNA is targeted to p21/Waf-1.

2. The method of claim 1, wherein the prostate cells are exposed to a radiation treatment prior to, simultaneous with or following contact with the adenovirus construct.

3. A method for enhancing oncolytic adenovirus replication in prostate cells comprising: contacting the prostate cells with a composition comprising an adenovirus construct and a pharmaceutically acceptable carrier, wherein the adenovirus construct comprises a nucleic acid sequence encoding an shRNA in the E1 region or the Fiber region; and a nucleic acid sequence encoding a prostate specific promoter or a prostate specific enhancer, wherein the shRNA is targeted to p21/Waf-1.

4. The method of claim 3, wherein the prostate cells are exposed to a radiation treatment prior to, simultaneous with or following contact with the composition.

5. A method for treating a subject having prostate cancer comprising: administering to the subject a therapeutically effective amount of an adenovirus construct comprising a nucleic acid sequence encoding an shRNA in the E1 region or the Fiber region; and a nucleic acid sequence encoding a prostate specific promoter or a prostate specific enhancer, wherein the shRNA is targeted to p21/Waf-1.

6. The method of claim 5, wherein the subject is exposed to a radiation treatment prior to, simultaneous with or following contact with the adenovirus construct.

7. A method for treating a subject having prostate cancer comprising: administering to the subject a therapeutically effective amount of a composition comprising an adenovirus construct and a pharmaceutically acceptable carrier, wherein the adenovirus construct comprises a nucleic acid sequence encoding an shRNA in the E1 region or the Fiber region; and a nucleic acid sequence encoding a prostate specific promoter or a prostate specific enhancer, wherein the shRNA is targeted to p21/Waf-1.

8. The method of claim 7, wherein the subject is exposed to a radiation treatment prior to, simultaneous with or following contact with the composition.

9. The method of any of claim 5, 6, 7, or 8, wherein the subject is a human patient.

10. A method for selectively lysing a neoplastic prostate cell comprising: contacting the cell with an effective amount of an adenovirus construct comprising a nucleic acid sequence encoding an shRNA in the E1 region or the Fiber region; and a nucleic acid sequence encoding a prostate specific promoter or a prostate specific enhancer, wherein the shRNA is targeted to p21/Waf-1.

11. The method of claim 10, wherein the cell is exposed to a radiation treatment prior to, simultaneous with or following contact with the adenovirus construct.

12. A method for selectively lysing a neoplastic prostate cell comprising: contacting the cell with an effective amount of a composition of comprising an adenovirus construct and a pharmaceutically acceptable carrier, wherein the adenovirus construct comprises a nucleic acid sequence encoding an shRNA in the E1 region or the Fiber region; and a nucleic acid sequence encoding a prostate specific promoter or a prostate specific enhancer, wherein the shRNA is targeted to p21/Waf-1.

13. The method of claim 12, wherein the cell is exposed to a radiation treatment prior to, simultaneous with or following contact with a composition.

* * * * *